US011809621B2

(12) United States Patent
Iwase et al.

(10) Patent No.: US 11,809,621 B2
(45) Date of Patent: Nov. 7, 2023

(54) STATE ESTIMATION DEVICE, METHOD AND COMPUTER PROGRAM THEREFOR

(71) Applicant: Mazda Motor Corporation, Hiroshima (JP)

(72) Inventors: Koji Iwase, Aki-gun (JP); Kazuo Sakamoto, Aki-gun (JP); Akihide Takami, Aki-gun (JP)

(73) Assignee: MAZDA MOTOR CORPORATION, Hiroshima (JP)

( * ) Notice: Subject to any disclaimer, the term of this patent is extended or adjusted under 35 U.S.C. 154(b) by 387 days.

(21) Appl. No.: 17/178,275

(22) Filed: Feb. 18, 2021

(65) Prior Publication Data
US 2021/0290128 A1   Sep. 23, 2021

(30) Foreign Application Priority Data

Mar. 19, 2020  (JP) ................................ 2020-049974

(51) Int. Cl.
*G06F 3/01*  (2006.01)
*A61B 5/16*  (2006.01)
(Continued)

(52) U.S. Cl.
CPC .............. *G06F 3/013* (2013.01); *A61B 5/162* (2013.01); *A61B 5/163* (2017.08); *A61B 5/6898* (2013.01); *G06F 3/0481* (2013.01); *G06V 20/10* (2022.01); *G06V 40/18* (2022.01); *A61B 5/0022* (2013.01); *A61B 5/0077* (2013.01); *A61B 5/7435* (2013.01);
(Continued)

(58) Field of Classification Search
CPC ....... G06F 3/013; G06F 3/0481; A61B 5/162; A61B 5/163; A61B 5/6898; A61B 5/0022; A61B 5/0077; A61B 5/7435; A61B 5/7475; A61B 5/168; G06V 20/10; G06V 40/18; G06V 2201/02; G06N 5/041

See application file for complete search history.

(56) References Cited

U.S. PATENT DOCUMENTS 7,762,665 B2 *  7/2010  Vertegaal .................. G06F 3/14
                                                351/209
10,162,651 B1 *  12/2018  Zhu .......................... G06F 9/453
(Continued)

FOREIGN PATENT DOCUMENTS

JP    2016-103102 A    6/2016

*Primary Examiner* — Eric F Winakur
*Assistant Examiner* — Jonathan Drew Moroneso
(74) *Attorney, Agent, or Firm* — XSENSUS LLP

(57) ABSTRACT

A state of a user of a mobile terminal having a display for displaying an image may be estimated. A sightline detector detects a sightline of the user of a mobile terminal and processing circuitry is configured to estimate a state of the user. The processing circuitry is configured to determine a top-down index value that is correlated with an attention source amount allocated to top-down attention of the user with respect to an image displayed on a display of the mobile terminal. The processing circuitry is configured to determine a bottom-up index value correlated with the attention source amount allocated to bottom-up attention of the user with respect to the image displayed on the display. The processing circuitry is configured to estimate the user state including an attention function degraded state based on the top-down index value and the bottom-up index value.

14 Claims, 20 Drawing Sheets

(51) Int. Cl.
*A61B 5/00* (2006.01)
*G06V 20/10* (2022.01)
*G06V 40/18* (2022.01)
*G06F 3/0481* (2022.01)

(52) U.S. Cl.
CPC ........ *A61B 5/7475* (2013.01); *G06V 2201/02* (2022.01)

(56) References Cited

U.S. PATENT DOCUMENTS

| | | | |
|---|---|---|---|
| 2015/0112224 A1* | 4/2015 | Super | A61B 3/02 600/558 |
| 2017/0192502 A1* | 7/2017 | Dmitrieva | G11B 27/007 |
| 2018/0362053 A1* | 12/2018 | Isa | A61B 5/18 |
| 2020/0335065 A1* | 10/2020 | Furuta | G06F 3/013 |
| 2021/0041945 A1* | 2/2021 | Cooper | G06T 7/11 |

* cited by examiner

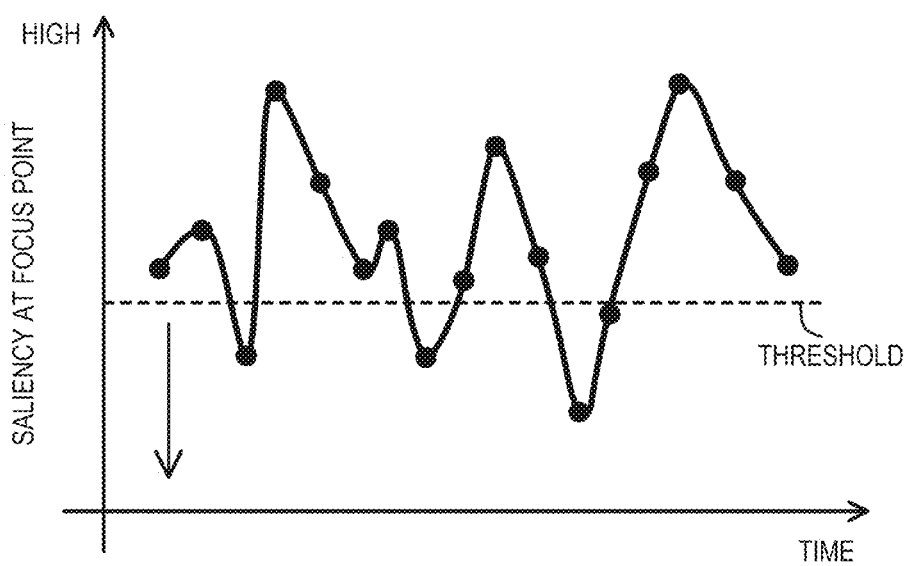

STATE ESTIMATION DEVICE, METHOD AND COMPUTER PROGRAM THEREFOR

CROSS REFERENCE TO RELATED APPLICATIONS

The present application contains subject matter related to Japanese Priority Application 2020-049974, filed in the Japanese Patent Office on Mar. 19, 2020, the entire contents of which being incorporated herein by reference in its entirety. The application also contains subject matter related to that described in U.S. application Ser. No. xx/xxx,xxx, having and claiming priority to JP 2020-049973.

TECHNICAL FIELD

A technique disclosed herein relates to a state estimation device.

BACKGROUND ART

A mobile terminal is disclosed in Patent document 1. This mobile terminal includes: a display section that displays plural objects for an input operation on a main surface; a movement detection section that detects movement; an image acquisition section that acquires an image; a sightline position detection section; and a control section. The sightline position detection section detects a sightline position of a user that corresponds to any of the plural objects based on the image that is acquired by the image acquisition section. Of the plural objects, the control section confirms, as a target object, the object that is displayed at a first sightline position detected by the sightline position detection section. In addition, in the case where the movement detection section detects movement in a horizontal direction with respect to the main surface of the display section, the control section confirms, as a second sightline position, the sightline position that is detected by the sightline position detection section after the movement in the horizontal direction is detected. Then, in the case where a distance between the first sightline position and the second sightline position is equal to or longer than a threshold, the control section changes a display position of the target object based on the second sightline position.

PRIOR ART DOCUMENTS

Patent Documents

[Patent document 1] JP-A-2016-103102

SUMMARY

Problems to be Solved

By the way, it is considered to estimate a state of the mobile terminal user including an attention function degraded state to improve a function of the mobile terminal as in Patent document 1, and the like. However, a method for estimating the state of the mobile terminal user has not conventionally been discussed.

A technique disclosed herein has been made in view of such a point and therefore has a purpose of estimating a state of a user of a mobile terminal.

Means for Solving the Problems

A technique disclosed herein relates to a state estimation device that estimates a state of a user of a mobile terminal having a display section for displaying an image. This state estimation device includes: a sightline detector that detects the user's sightline; and processing circuitry that estimates the state of the user. The processing circuitry is configured to determine a top-down index value based on the image displayed on the display section and the user's sightline detected by the sightline detection section, the top-down index value being correlated with an attention source amount that is allocated to top-down attention of the user with respect to the image determine a bottom-up index value based on the image displayed on the display section and the user's sightline detected by the sightline detector, the bottom-up index value being correlated with the attention source amount that is allocated to bottom-up attention of the user with respect to the image; and estimate the user state including an attention function degraded state based on the top-down index value measured by the top-down measurement section and the bottom-up index.

A technique disclosed herein relates to a method of estimating a state of a user of a mobile terminal having a display for displaying an image. The method includes detecting a sightline of the user; determining a top-down index value based on the image displayed on the display and the sightline of the user detected by the sightline detector, the top-down index value being correlated with an attention source amount that is allocated to top-down attention of the user with respect to the image on the display; determining a bottom-up index value based on the image displayed on the display and the sightline of the user detected by the sightline detection, the bottom-up index value being correlated with the attention source amount that is allocated to bottom-up attention of the user with respect to the image on the display; and estimating the state of the user including an attention function degraded state based on the top-down index value and the bottom-up index value.

A technique disclosed herein relates to a non-transitory computer readable storage device having computer readable instructions that when executed by a controller including a computer cause the computer to execute a state of a user of a mobile terminal estimation method. The method includes detecting a sightline of the user; determining a top-down index value based on the image displayed on the display and the sightline of the user detected by the sightline detector, the top-down index value being correlated with an attention source amount that is allocated to top-down attention of the user with respect to the image on the display; determining a bottom-up index value based on the image displayed on the display and the sightline of the user detected by the sightline detection, the bottom-up index value being correlated with the attention source amount that is allocated to bottom-up attention of the user with respect to the image on the display; and estimating the state of the user including an attention function degraded state based on the top-down index value and the bottom-up index value.

As a result of study, the inventors of the present application determined that there was a correlation between the motion of the user's sightline with respect to the image displayed on the display section and the user state (particularly, a state related to an attention function). Furthermore, the inventors of the present application found that there was a correlation between degradation of the attention function of the user and each of the attention source amount allocated to the top-down attention of the user (hereinafter described as a "top-down attention source amount") and the attention source amount that is allocated to the bottom-up attention of the user (hereinafter described as a "bottom-up attention source amount"). Thus, by executing the first estimation processing, the user state including the attention function degraded state based on the top-down attention source amount and the bottom-up attention source amount of the user with respect to the image displayed on the display section may be estimated.

In the state estimation device, the top-down measurement section may have: a point of interest detection section that detects a point of interest in the image displayed on the display section in the first estimation processing; and a top-down index deriving section that derives the top-down index value based on motion of the user's sightline with respect to the point of interest in the image in the first estimation processing.

In the configuration, it is possible to appropriately derive the top-down index value based on the motion of the user's sightline with respect to the point of interest in the image displayed on the display section. As a result, it is possible to appropriately estimate the user state.

In the state estimation device, the bottom-up measurement section may have: a saliency detection section that detects distribution of saliency in the image displayed on the display section in the first estimation processing; and a bottom-up index deriving section that derives the bottom-up index value based on motion of the user's sightline with respect to the distribution of the saliency in the image in the first estimation processing.

In the configuration, it is possible to appropriately derive the bottom-up index value based on the motion of the user's sightline with respect to the distribution of saliency in the image displayed on the display section. As a result, the user state may be appropriately estimated.

In the state estimation device, the estimation section may be configured that, in the case where the top-down index value falls below a predetermined top-down threshold, the estimation section estimates that the user is in a first attention function degraded state when the bottom-up index value does not fall below a predetermined bottom-up threshold, and the estimation section estimates that the user is in a second attention function degraded state, in which an attention function is degraded in comparison with that in the first attention function degraded state, when the bottom-up index value falls below the bottom-up threshold.

In the configuration, it is possible to distinguish the first attention function degraded state and the second attention function degraded state from each other for evaluation. As a result, it is possible to appropriately estimate the user state.

In the state estimation device, the estimation processing section may be configured to execute the first estimation processing and second estimation processing to estimate the user state based on a cognitive response time of the user.

In the configuration, it is possible to execute the second estimation processing to estimate the user state based on the cognitive response time of the user in addition to the first estimation processing to estimate the user state based on the motion of the user's sightline with respect to the image displayed on the display section. As a result, the user state may be appropriately estimated.

In the state estimation device, the estimation processing section may be configured to selectively execute the first estimation processing or the second estimation processing according to likeliness of occurrence of bottom-up attention of the user with respect to the image displayed on the display section.

In the configuration, likeliness of occurrence of the user's bottom-up attention with respect to the image displayed on the display section is considered. Thus, it is possible to appropriately execute the first estimation processing to estimate the user state based on the motion of the user's sightline with respect to the image displayed on the display section and the processing to estimate the user state based on the cognitive response time of the user. As a result, it is possible to appropriately estimate the user state.

According to the technique disclosed herein, it is possible to estimate the state of the user of the mobile terminal.

BRIEF DESCRIPTION OF THE DRAWINGS

FIG. 13 is a graph of a change in the saliency at a focus point.

FIG. 14 is a graph of a change in the saliency at a random point.

DETAILED DESCRIPTION

Figure 1:
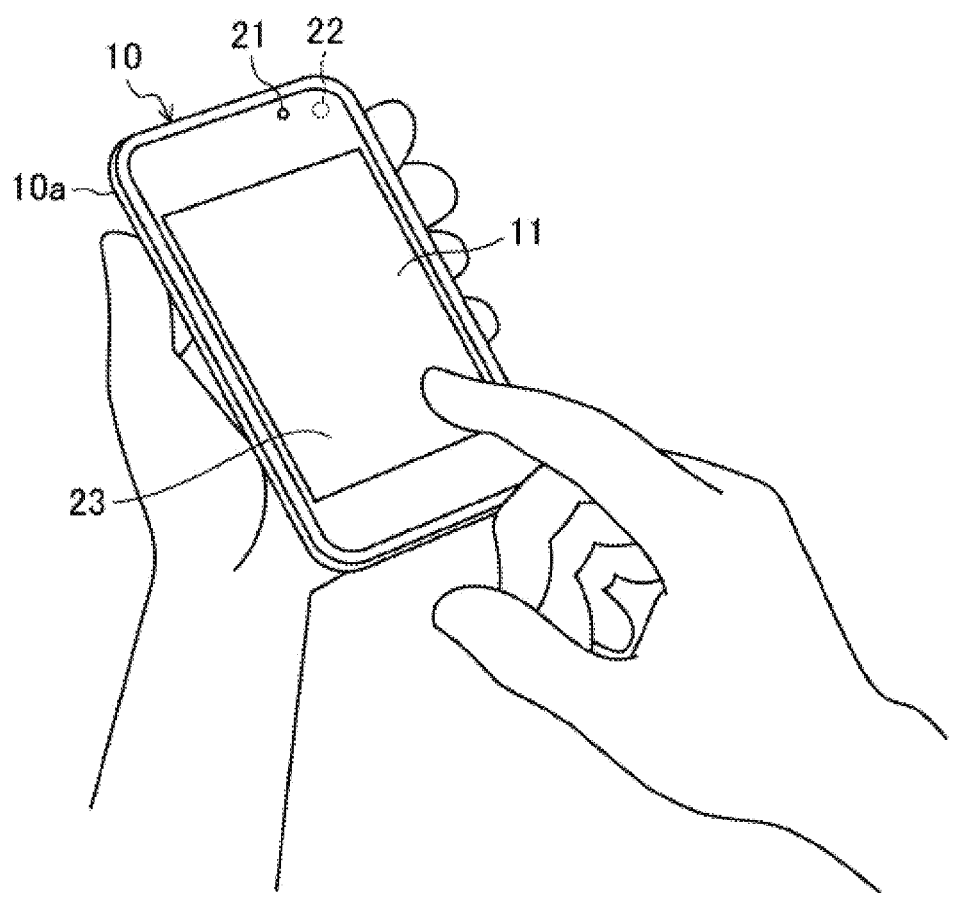
FIG. 1 is a perspective view of external appearance of a mobile terminal according to an embodiment.

A detailed description will hereinafter be made on an embodiment with reference to the drawings. The same or corresponding portions in the drawings will be denoted by the same reference signs and numerals and the description thereon will not be repeated.

(Embodiment)

Figure 2:
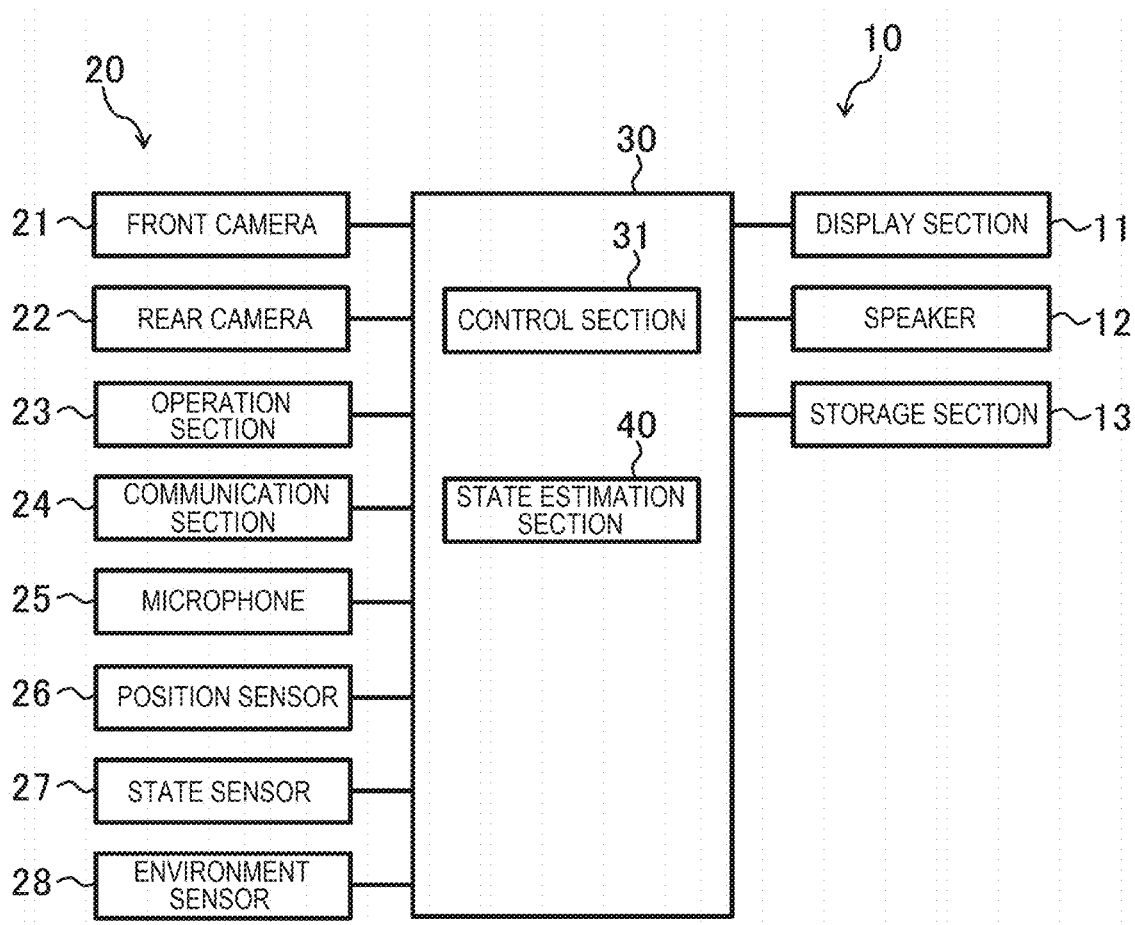
FIG. 2 is a block diagram of a configuration of the mobile terminal according to the embodiment.
Figure 3:
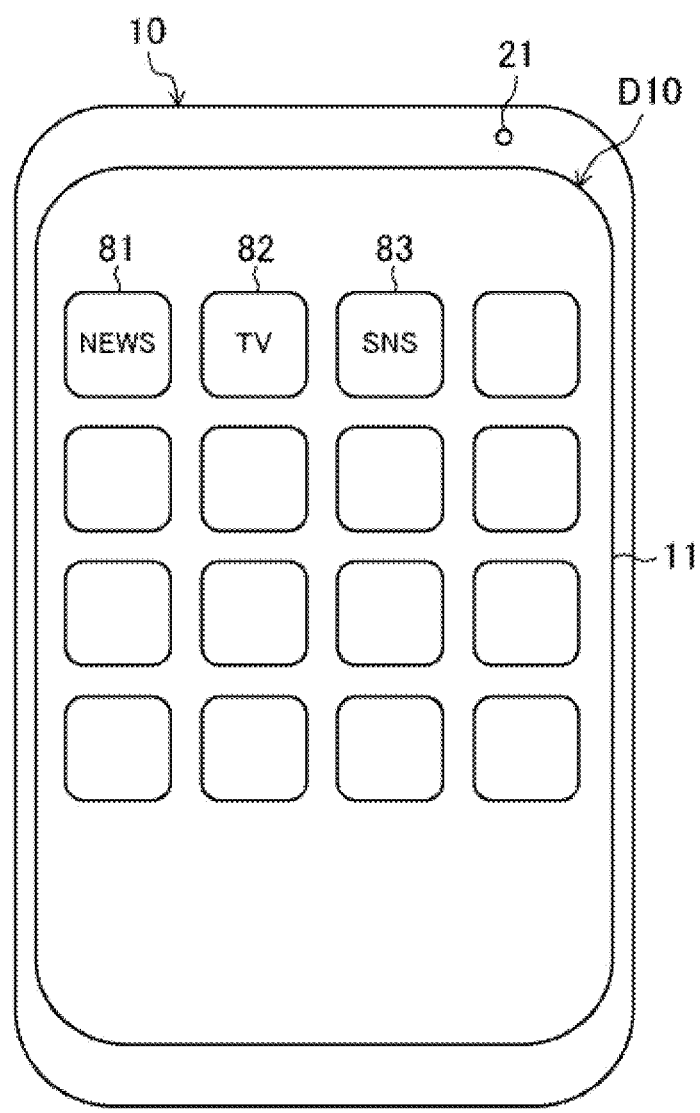
FIG. 3 is a view of an app selection image that is displayed on a display section.

FIG. 1 and FIG. 2 illustrate external appearance and a configuration of a mobile terminal 10 according to an embodiment. The mobile terminal 10 is held by a user's hand and is operated. In this example, the mobile terminal 10 constitutes a smartphone. More specifically, the mobile terminal 10 includes a casing 10a, a display section 11, a speaker 12, a storage section 13, e.g., a memory, an information acquisition section 20, and a controller 30. Hereinafter, the user of the mobile terminal 10 will simply be described as a "user".

[Casing]

The casing 10a may have a flat rectangular parallelepiped shape. The casing 10a accommodates components of the mobile terminal 10.

[Display Section, Speaker, and Storage Section]

The display section 11 displays an image. The display section 11 may have a rectangular plate shape, and is on a front surface of the casing 10a. The speaker 12 plays a audio information. The storage section 13 stores various types of information and data. In this example, the storage section 13 stores programs of various applications that can be executed in the mobile terminal 10. Hereinafter, the application will be described as an "app". Examples of such an app are a news app, a television app, a social networking service (SNS) app, or the like.

[Information Acquisition Section]

The information acquisition section 20 acquires the various types of the information that are used in the mobile terminal 10. In this example, the information acquisition section 20 includes a front camera 21, a rear camera 22, an operation section 23, a communication section 24, a microphone 25, a location sensor 26, a state sensor 27, and an environment sensor 28. Each camera may have an image sensor that takes fixed and/or moving images in the visual spectrum and/or non-visual ranges such as infrared and ultraviolet. Each camera may have wide-angle lens and/or a narrow angle lens. Each camera may be monocular or stereo.

<Front Camera>

The front camera 21 is provided on the front surface of the casing 10a. The front camera 21 captures an image of a front region that broadens in front of the mobile terminal 10, and thereby acquires the image that shows the front region of the mobile terminal 10. With such a configuration, the front camera 21 can acquire an image including the user's face (particularly, eyeballs). For example, the front camera 21 performs imaging operation in a state where the mobile terminal 10 is held by the user's hand such that the front camera 21 opposes the user's face. In this way, the image including the user's face is acquired. The image (image data) that is acquired by the front camera 21 is transmitted to the controller 30. For example, the front camera 21 is configured by using solid-state imaging elements such as a charge-coupled device (CCD) and a complementary metal-oxide-semiconductor (CMOS).

<Rear Camera>

The rear camera 22 is provided on a rear surface of the casing 10a. The rear camera 22 captures an image of a rear region that broadens behind the mobile terminal 10, and thereby acquires the image that shows the rear region of the mobile terminal 10. With such a configuration, the rear camera 22 can acquire an image including surrounding environment that broadens around the user (in this example, front environment that broadens in front of the user). For example, the rear camera 22 performs the imaging operation in a state where the mobile terminal 10 is held by the user's hand such that the rear camera 22 opposes the front environment. In this way, the image including the front environment of the user is acquired. The image (image data) that is acquired by the rear camera 22 is transmitted to the controller 30. For example, the rear camera 22 is configured by using the solid-state imaging elements such as the CCD and the CMOS.

<Operation Section>

The operation section 23 is operated by the user and outputs a signal corresponding to an operation given by the user. With such a configuration, the user can operate the operation section 23 to input information. The output of the operation section 23 is transmitted to the controller 30. In this example, the operation section 23 includes a touch operation section that constitutes, with the display section 11, a touchscreen. The operation section 23 may include an operation dial, an operation button, or the like in addition to the touch operation section.

<Communication Section>

The communication section 24 receives various types of information and various types of data through a communication network (for example, the Internet, a mobile-phone line, or the like) that is provided on the outside of the mobile terminal 10. For example, the communication section 24 receives voice data, image data, map information, and the like from another information terminal. The information and the data acquired by the communication section 24 are transmitted to the controller 30.

The above map information may be three-dimensional map information such as a dynamic map. For example, the map information includes: road map data on a road such as a sidewalk; and object information on an object. The road map data includes information on a road shape, a road structure, a road gradient, a lane marking, a road surface marking, and the like. The object information includes stationary object information and mobile object information. The stationary object information is information on a stationary object that is not displaced over time. The stationary object information includes information on a shape of the stationary object, positional coordinates of the stationary object, and the like. Examples of the stationary object are a road sign and a structure. Examples of the structure are a traffic light, a median strip, a center pole, a building, a signboard, a level crossing, a tunnel, a railway track bed, and a bus stop. The mobile object information is information on a mobile object that is possibly displaced over time. The mobile object information includes information on a shape of the mobile object, positional coordinates of the mobile object, a speed of the mobile object, and the like. Examples of the mobile object are a vehicle and a pedestrian.

<Microphone>

The microphone 25 converts the voice into an electric signal. The electric signal (the voice data) that is acquired by the microphone 25 is transmitted to the controller 30.

<Location Sensor>

The location sensor 26 detects a location (for example, a latitude and a longitude) of the mobile terminal 10. For example, the location sensor 26 receives GPS information from the Global Positioning System and detects the location of the mobile terminal 10 based on the GPS information. The information (the location of the mobile terminal 10) that is acquired by the location sensor 26 is transmitted to the controller 30.

<State Sensor>

The state sensor 27 detects a state (for example, acceleration, an angular velocity, a posture, and the like) of the mobile terminal 10. For example, the state sensor 27 includes an acceleration sensor, a gyroscope sensor, and the like. The information (the state of the mobile terminal 10) that is acquired by the state sensor 27 is transmitted to the controller 30.

<Environment Sensor>

The environment sensor 28 detects information (for example, light, magnetism, and the like) on environment that broadens around the mobile terminal 10. For example, the environment sensor 28 includes an optical sensor, a magnetic sensor, a proximity sensor, and the like. The information acquired by the environment sensor 28 (information on the surrounding environment of the mobile terminal 10) is transmitted to the controller 30.

[Controller]

The controller 30 is connected to each section (in this example, the display section 11, the speaker 12, the storage section 13, and the information acquisition section 20) of the mobile terminal 10 in a manner capable of transmitting a signal. Then, the controller 30 controls each of the sections of the mobile terminal 10 based on the information acquired by each of the sections of the mobile terminal 10. The controller 30 is an example of the state estimation device.

For example, the controller 30 is constructed of one or plural integrated circuits (ICs). In the IC, a single core or die may be provided, or plural cooperative cores or dies may be provided. For example, the core or the die may include a processor (a CPU) and memory that stores a program for operating the CPU and information such as a processing result by the CPU.

The controller 30 includes a control section 31 and a state estimation section 40. Optionally, the controller 30 may include a processor 835 and other circuitry in system 800 of FIG. 23, which may be implemented as a single processor-based system, or a distributed processor-based system, including remote processing, such as cloud-based processing.

<Control Section>

The control section 31 controls each of the sections of the mobile terminal 10 based on the various types of the information and the various types of the data that are acquired by the sections of the mobile terminal 10. In addition, the control section 31 executes the program of the app stored in the storage section 13 to perform operation according to the app.

For example, the control section 31 stores the information and the data, which are acquired by the information acquisition section 20, in the storage section 13. In addition, the control section 31 executes display control, telephone call control, and the like. In the display control, the control section 31 outputs the image data to the display section 11. The display section 11 plays the image indicated by the image data. In the telephone call control, the control section 31 outputs the voice data, which is acquired by the communication section 24, to the speaker 12. The speaker 12 plays the voice data. The control section 31 transmits the voice data, which is acquired by the microphone 25, to the communication network through the communication section 24.

<State Estimation Section>

The state estimation section 40 estimates the user state. A detailed description on the state estimation section 40 will be made below.

[Description of Terms]

Next, a description will be made on terms used in the following description. In the following description, terms such as an attention source, top-down attention, a top-down attention source amount, a top-down attention demand amount, bottom-up attention, a bottom-up attention source amount, a bottom-up attention demand amount, a task demand, a point of interest, saliency, a cognitive response time, an attention function degraded state, a motor function degraded state, a cognitive motor function degraded state, and a normal state are used and are defined below.

<Attention Source>

The attention source is a concept that represents attentiveness of a person in a quantitative manner. The attentiveness of the person can be considered a limited resource. In the case where an attention source amount that is allocated to attention to a certain target is insufficient, the attentiveness of the person cannot fully be exerted on such a target, and the attention of the person to such a target becomes insufficient.

<Top-Down Attention>

The top-down attention is an attention mechanism in which the person actively moves his/her sightline to an intended point. For example, in the case where the person has previous knowledge on a stimulus to be selected, the person can actively bias points to select the intended stimulus.

<Top-Down Attention Source Amount and Top-Down Attention Demand Amount>

The top-down attention source amount is the amount of the attention source that is allocated to the top-down attention. The top-down attention demand amount is the attention source amount that is requested for the top-down attention. In the case where the top-down attention source amount falls below the top-down attention demand amount, the top-down attention becomes insufficient.

<Bottom-Up Attention>

The bottom-up attention is an attention mechanism in which the person's sightline is passively attracted to a noticeable point. For example, in the case where, of plural visual stimuli, the single stimulus significantly differs from the stimuli therearound, in the case where the visual stimulus suddenly appears, or the like, the person's sightline is passively attracted to such a stimulus.

<Bottom-Up Attention Source Amount and Bottom-Up Attention Demand Amount>

The bottom-up attention source amount is the amount of the attention source that is allocated to the bottom-up attention. The bottom-up attention demand amount is the attention source amount that is requested for the bottom-up attention. In the case where the bottom-up attention source amount falls below the bottom-up attention demand amount, the bottom-up attention becomes insufficient.

<Task Demand>

The task demand is a difficulty of a task imposed on the person. As the difficulty of the task is increased, the task demand is increased. Examples of the task are an operation task of operating the mobile terminal 10 while checking the display of the mobile terminal 10 and a walking task of walking while checking the display of the mobile terminal 10. Examples of the operation performed in the operation task are reading of a news article, viewing of a television video, reading of a message, visual recognition of an icon, and selection of the icon. Examples of the operation performed in the walking task are monitoring of a situation, avoidance of danger, compliance with traffic rules, and a destination search.

<Point of Interest>

The point of interest is a point to which the person should pay attention to achieve the task, and a point to which the person should intentionally turn his/her sightline in the top-down attention. Examples of the point of interest are the point of interest in the image displayed on the display section 11 and the point of interest in the surrounding environment of the user.

The point of interest in the image displayed on the display section 11 is the point to which the user should pay attention to achieve the operation task. Examples of the point of interest in the image displayed on the display section 11 are a point of information at which information relevant to the operation task is displayed and an operation point that should be visually recognized for the operation of the mobile terminal 10. An example of the point of information is a point with a valuable meaning.

The point of interest in the surrounding environment of the user is a point to which the user should pay attention to achieve the walking task. Examples of the point of interest in the surrounding environment of the user are a walking information point at which information relevant to the walking task is displayed and a visual recognition requested point that should visually be recognized for the user to walk safely. Examples of the walking information point are the traffic light, the road sign, and the road surface marking. Examples of the visual recognition requested point are another pedestrian and the vehicle.

The point of interest may be defined empirically. For example, an intersection into which the pedestrian is predicted to run may be set as the point of interest in the surrounding environment of the user.

<Saliency>

The saliency is a value indicative of a degree of the visual stimulus that attracts the bottom-up attention and is a value that varies by characteristics such as a color, luminance, a direction, and motion. For example, as a difference in the characteristic such as the color, the luminance, the direction, or the motion between a certain area included in the image and a surrounding area increases, the visual stimulus that attracts the bottom-up attention increases, and the saliency in such a certain area increases. As the saliency at a certain point included in the image is increased, the person's sightline is more likely to be attracted to such a certain point.

Hereinafter, a point at which the saliency is relatively high will be described as the "high visibility point", and a point at which the saliency is relatively low will be described as the "low visibility point". For example, the high visibility point is a point at which the saliency exceeds a predetermined saliency reference value, and the low visibility point is a point at which the saliency falls below the saliency reference value.

Hereinafter, a proportion of the high visibility point in the image will be described as the "high visibility proportion". For example, the high visibility proportion is a value that is acquired by dividing a total area of the high visibility point included in the image by a total area of the image. In addition, hereinafter, the image with the relatively high visibility proportion will be described as the "high visibility image", and the image with the relatively low visibility proportion will be described as the "low visibility image". For example, the high visibility image is an image, the high visibility proportion of which exceeds a predetermined high visibility proportion threshold, and the low visibility image is an image, the high visibility proportion of which does not exceed the high visibility proportion threshold. The high visibility image is an image with which the bottom-up attention is relatively likely to occur. The low visibility image is an image with which the bottom-up attention is relatively less likely to occur.

<Cognitive Response Time>

The cognitive response time is a time required for the person to take action after acknowledgement. An example of the cognitive response time is a time that is required from time at which the person visually recognizes a particular point in the image displayed on the display section 11 to time at which the person gives an operation (for example, a touch operation) of selecting the particular point to the operation section 23. Examples of the particular point are the icon and a character included in a dial.

<Attention Function Degraded State>

The attention function degraded state is a state where an attention function of the person is degraded. The attention function degraded state is detrimental to the operation of the mobile terminal 10 by the user. The attention function degraded state includes: a first attention function degraded state that is a mild degree of the attention function degraded state; and a second attention function degraded state that is a severe degree of the attention function degraded state.

The first attention function degraded state is the attention function degraded state that can be recovered to the normal state by resting or the like. Examples of the first attention function degraded state are wakefulness degradation, fatigue, and a drifted state.

The second attention function degraded state is a state where the attention function of the person is more degraded than that in the first attention function degraded state. In addition, the second attention function degraded state is the state that cannot easily be recovered to the normal state by resting or the like. An example of the second attention function degraded state is a disease that is accompanied by the degraded attention function. Examples of the disease accompanied by the degraded attention function are a cardiac disorder such as myocardial infarction, a brain disorder such as a cerebral stroke, epilepsy, and hypoglycemia.

<Motor Function Degraded State and Cognitive Motor Function Degraded State>

The motor function degraded state is a state where a motor function of the person is degraded. In the motor function degraded state, abnormality is likely to occur to a walking pace and a tremor of a posture of the person. The cognitive motor function degraded state is a state where a cognitive motor function of the person is degraded. The cognitive motor function is a function of the person to acknowledge and take action. In the cognitive motor function degraded state, an erroneous operation is likely to occur.

<Normal State>

The normal state is a state where the abnormality as described above does not occur and the person can normally perform the operation to be performed. In the normal state, the user normally operates the mobile terminal 10.

[Image Displayed on Display Section]

Next, a description will be made on the image displayed on the display section 11 of the mobile terminal 10 with reference to FIG. 3 to FIG. 6. For example, the controller 30 displays an app selection image D10 illustrated in FIG. 3 on the display section 11. The app selection image D10 includes a news app icon 81, a television app icon 82, and an SNS app icon 83.

<Article Browsing Image>

Figure 4:
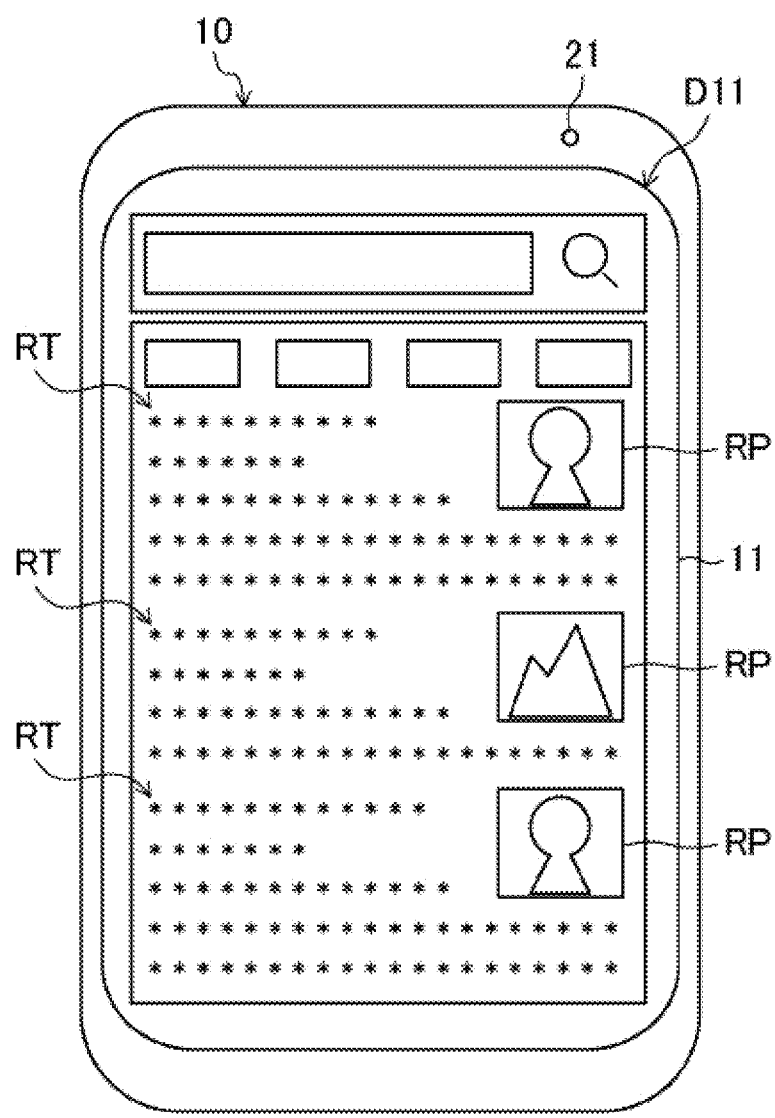
FIG. 4 is a view of an article browsing image of a news app.

When an operation to select the news app icon 81 included in the app selection image D10 is given to the operation section 23, the news app is run. Then, as illustrated in FIG. 4, an article browsing image D11 is displayed on the display section 11. The article browsing image D11 illustrated in FIG. 4 includes a text area RT and a picture area RP. In the text area RT, information with a valuable meaning such as an article is displayed. In the picture area RP, information with a less valuable meaning such as an advertisement is displayed. In the article browsing image D11 illustrated in FIG. 4, the point of interest and the high visibility point co-exist. In an example illustrated in FIG. 4, the text area RT corresponds to the point of interest, and the picture area RP corresponds to the high visibility point. The article browsing image D11 illustrated in FIG. 4 corresponds to the high visibility image (the image in which the proportion of the high visibility point is relatively high).

<Viewing Image>

Figure 5:
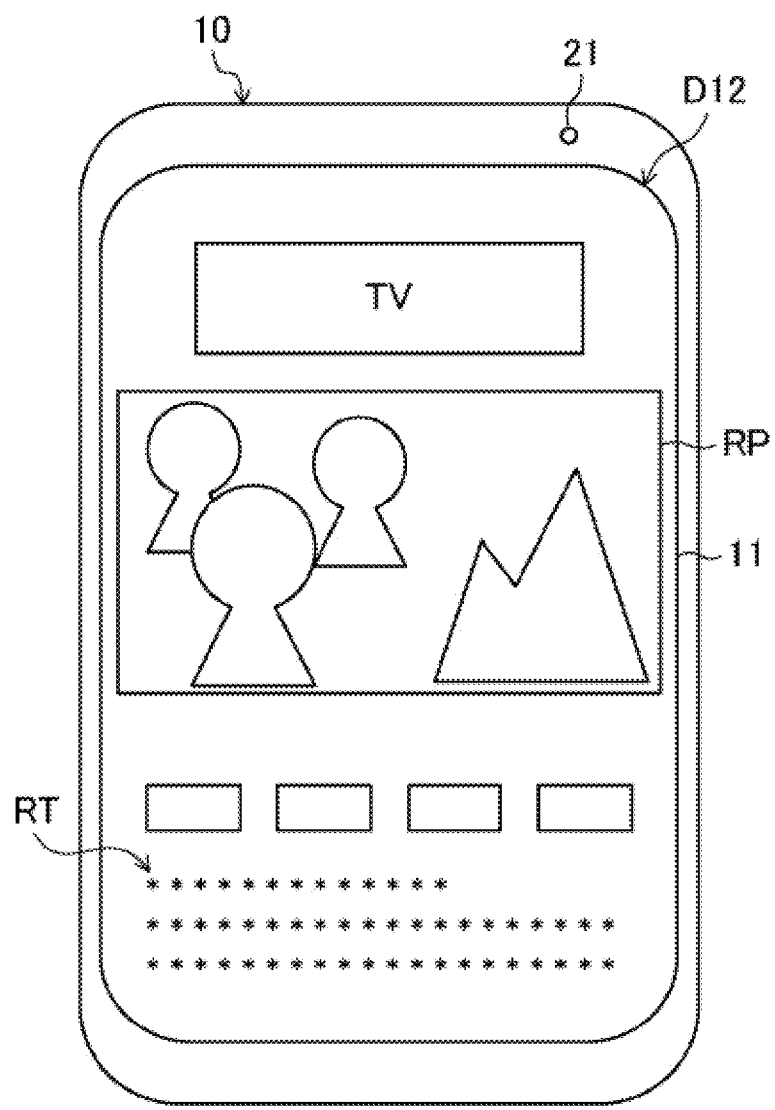
FIG. 5 is a view of a viewing image of a television app.

When an operation to select the television app icon 82 included in the app selection image D10 is given to the operation section 23, the television app is run. Then, as illustrated in FIG. 5, a viewing image D12 is displayed on the display section 11. The viewing image D12 illustrated in FIG. 5 includes the text area RT and the picture area RP. In the picture area RP, information with a valuable meaning such as a video of a television program is displayed. In the text area RT, information with a valuable meaning such as a description of the television program is displayed. The viewing image D12 may include a sub-picture area in which the information with the less valuable meaning such as the advertisement is displayed. In the viewing image D12 illustrated in FIG. 5, the points of interest and the high visibility points co-exist. In an example illustrated in FIG. 5, the text area RT corresponds to the point of interest, the picture area RP corresponds to both the point of interest and the high visibility point, and the sub-picture area corresponds to the high visibility point. The viewing image D12 illustrated in FIG. 5 corresponds to the high visibility image (the image in which the proportion of the high visibility point is relatively high).

<Message Reading Image>

Figure 6:
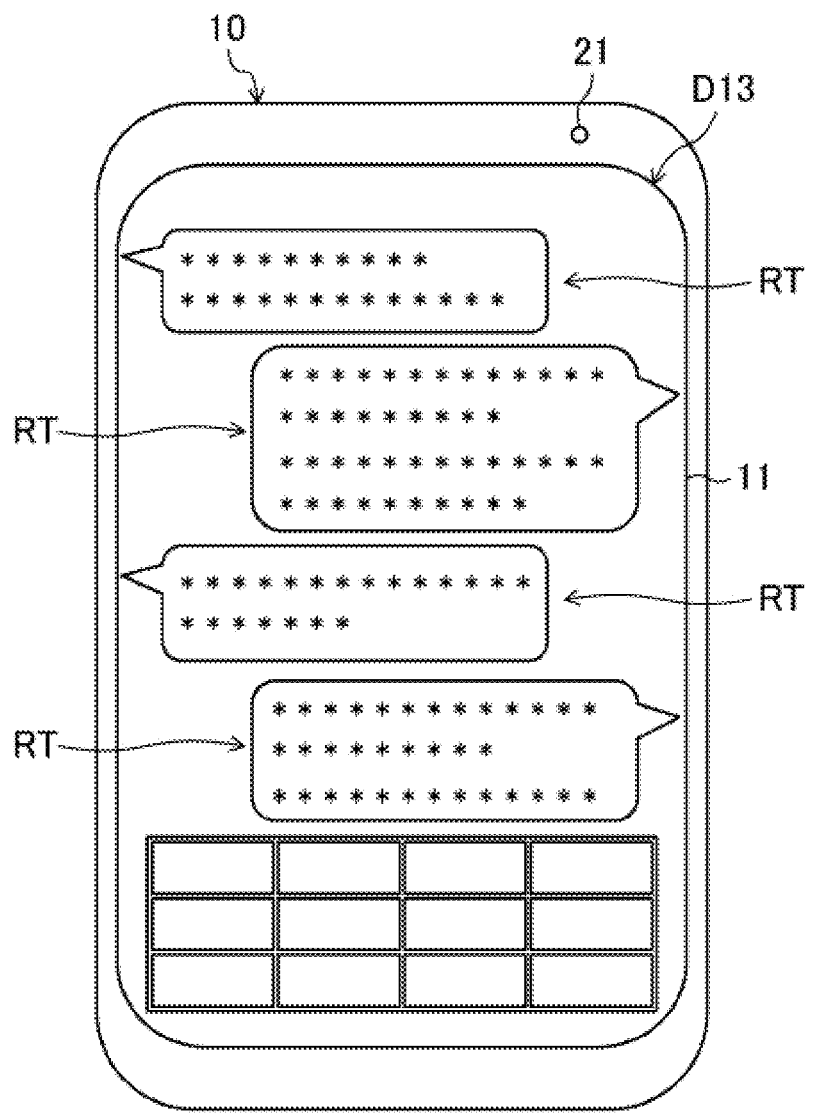
FIG. 6 is a view of a message reading image of an SNS app.

When an operation to select the SNS app icon 83 included in the app selection image D10 is given to the operation section 23, the SNS app is run. Then, as illustrated in FIG. 6, a message reading image D13 is displayed on the display section 11. The message reading image D13 illustrated in FIG. 6 includes the text area RT. In the text area RT, information with a valuable meaning such as a message body is displayed. In the message reading image D13 illustrated in FIG. 6, the point of interest and the high visibility point do not co-exist, and the point of interest is predominant. In an example illustrated in FIG. 6, the text area RT corresponds to an area of interest. The message reading image D13 illustrated in FIG. 6 corresponds to the low visibility image (the image in which the proportion of the high visibility point is relatively low).

Figure 7:
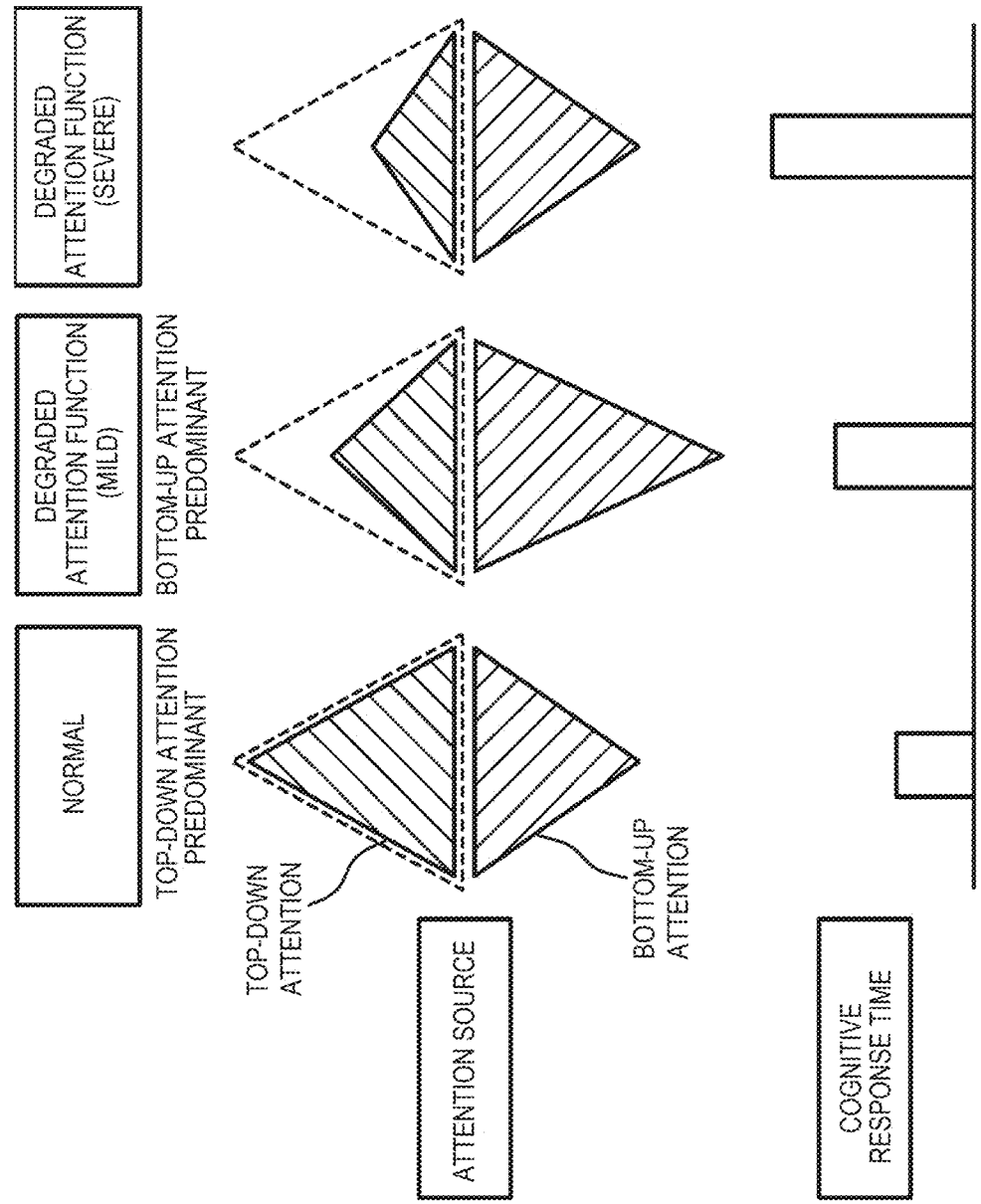
FIG. 7 is a view of a change in an attention source amount, which is allocated to each of top-down attention and bottom-up attention accompanied by degradation of an attention function, and a change in a cognitive response time.

As a result of study, the inventors of the present application determined that there was a correlation between motion of the user's sightline with respect to the image (or the surrounding environment of the user) displayed on the display section 11 and the user state (particularly, the state related to the attention function). More specifically, as illustrated in FIG. 7, the inventors of the present applicant found that the top-down attention source amount and the bottom-up attention source amount varied according to degradation of the attention function of the person such as the user. In an example illustrated in FIG. 7, a height of each up-pointing triangle with diagonal hatch lines from bottom left to top right indicates the top-down attention source amount. A height of each broken up-pointing triangle indicates the top-down attention demand amount. A height of each down-pointing triangle with diagonal hatch lines from bottom right to top left indicates the bottom-up attention source amount. In addition, as illustrated in FIG. 7, the inventors of the present application determined that the cognitive response time of the person varied according to the change in the attention function of the person.

Then, the inventors of the present application determined the following.

(1) When the state of the person is shifted from the normal state to the second attention function degraded state (the severe degree of the attention function degraded state), a total amount of the attention source of the person is reduced. More specifically, the top-down attention source amount is reduced, and the top-down attention source amount falls below the top-down attention demand amount. In addition, the bottom-up attention source amount is also reduced.

(2) When the state of the person is shifted from the normal state to the first attention function degraded state (the mild degree of the attention function degraded state), the top-down attention source amount is reduced, and the top-down attention source amount falls below the top-down attention demand amount. Meanwhile, the bottom-up attention source amount is increased by the reduced amount of the top-down attention source amount. On the contrary, when the state of the person is shifted from the first attention function degraded state (the mild degree of the attention function degraded state) to the normal state, the top-down attention source amount is increased, and the top-down attention source amount reaches the top-down attention demand amount. Meanwhile, the bottom-up attention source amount is reduced by the increased amount of the top-down attention source amount. The total amount of the attention source in the case where the state of the person is the first attention function degraded state is equal to the total amount of the attention source in the case where the state of the person is the normal state.

(3) The top-down attention source amount and the bottom-up attention source amount vary according to the task demand. More specifically, when the task demand is increased, the top-down attention demand amount is increased. As a result, the top-down attention source amount is increased, and the top-down attention source amount reaches the top-down attention demand amount. Meanwhile, the bottom-up attention source amount is reduced by the increased amount of the top-down attention source amount. On the contrary, when the task demand is reduced, the top-down attention demand amount is reduced. As a result, the top-down attention source amount is reduced, and the top-down attention source amount reaches the top-down attention demand amount. Meanwhile, the bottom-up attention source amount is increased by the reduced amount of the top-down attention source amount.

(4) When a top-down index value, which is correlated with the top-down attention source amount, is compared to a predetermined top-down threshold, the top-down attention source amount can be evaluated. The top-down threshold is set to a value that corresponds to the top-down attention demand amount. More specifically, as the top-down attention demand amount is increased, the top-down threshold is increased. For example, the top-down threshold is set to the top-down index value at the time when the top-down attention source amount matches the top-down attention demand amount. The top-down attention demand amount varies according to the task demand. More specifically, as the task demand is increased, the top-down attention demand amount is increased.

(5) When a bottom-up index value, which is correlated with the bottom-up attention source amount, is compared to a predetermined bottom-up threshold, the bottom-up attention source amount can be evaluated. The bottom-up threshold is set to a value that corresponds to the bottom-up attention demand amount. More specifically, as the bottom-up attention demand amount is increased, the bottom-up threshold is increased. For example, the bottom-up threshold is set to the bottom-up index value at the time when the bottom-up attention source amount matches the bottom-up attention demand amount. The bottom-up attention demand amount varies according to the task demand. More specifically, as the task demand is increased, the bottom-up attention demand amount is reduced. For example, the bottom-up attention demand amount is an amount that is acquired by subtracting the top-down attention demand amount from a predetermined attention demand total amount. For example, the attention demand total amount is a total amount of the attention source in the normal state.

(6) As the attention function of the person is reduced, the cognitive response time of the person is extended. More specifically, when the state of the person is shifted from the normal state to the first attention function degraded state (the mild degree of the attention function degraded state), the cognitive response time is extended. When the state of the person is shifted from the first attention function degraded state to the second attention function degraded state (the severe degree of the attention function degraded state), the cognitive response time is further extended.

(7) When the cognitive response time is compared to a predetermined time threshold (more specifically, a first time threshold and a second time threshold), the cognitive response time can be evaluated. For example, the first time threshold is set to the cognitive response time that is a boundary between the normal state and the first attention function degraded state. The second time threshold is set to the cognitive response time that is a boundary between the first attention function degraded state and the second attention function degraded state. Then, when the cognitive response time, the first time threshold, and the second time threshold are compared, the normal state, the first attention function degraded state, and the second attention function degraded state can be evaluated.

[Configuration of State Estimation Section]

Figure 8:
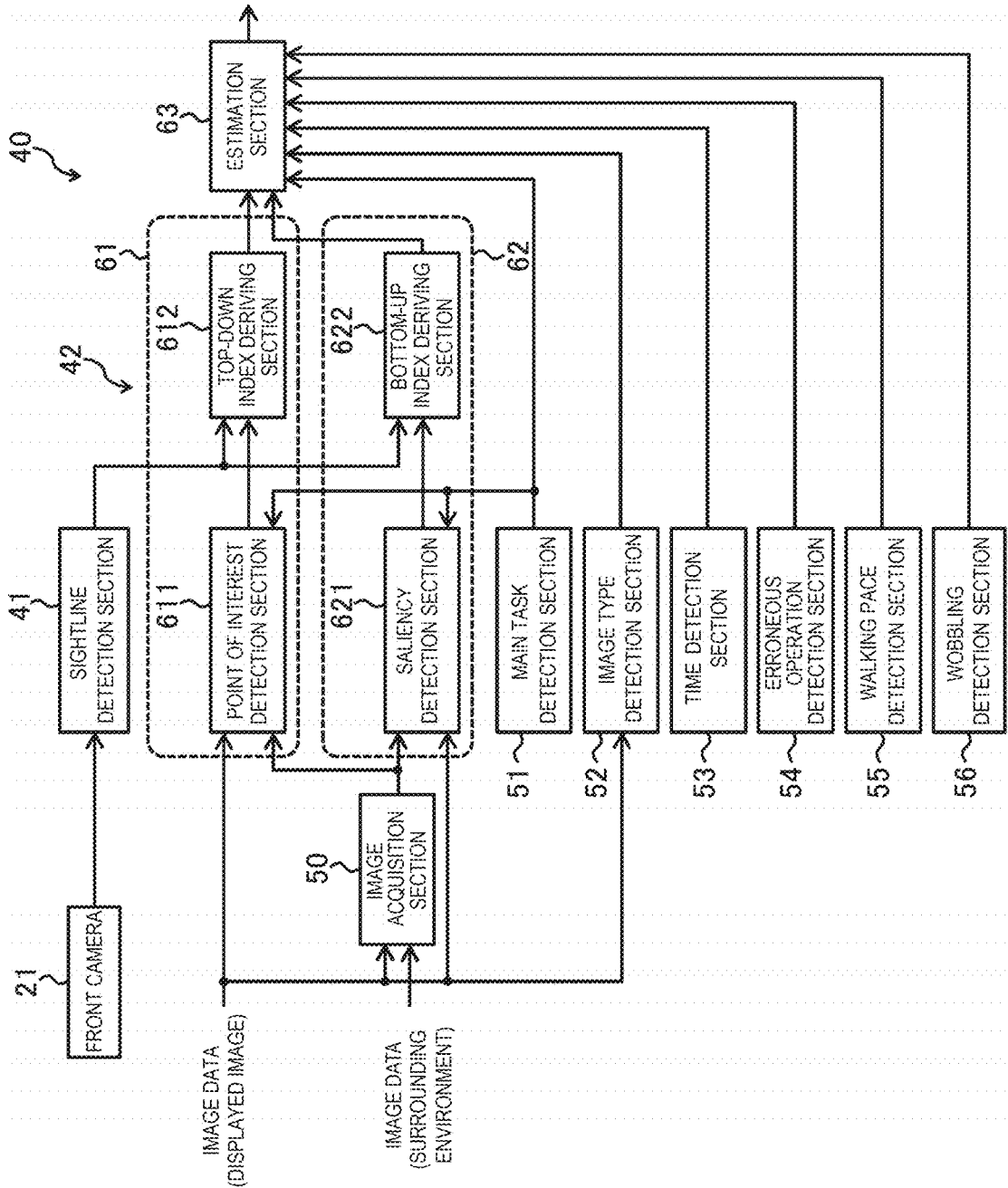
FIG. 8 is a block diagram of a configuration of a state estimation section.

FIG. 8 illustrates a configuration of the state estimation section 40. The state estimation section 40 has a sightline detection section 41, an estimation processing section 42, an image acquisition section 50, a main task detection section 51, an image type detection section 52, a time detection section 53, an erroneous operation detection section 54, a walking pace detection section 55, and a wobbling detection section 56.

[Sightline Detection Section]

The sightline detection section 41 detects the user's sightline. In this example, the sightline detection section 41 executes sightline detection processing on the image (the image including the user's face) that is acquired by the front camera 21, and thereby detects the user's sightline. This sightline detection processing may be processing that is executed by using a learning model generated by deep learning (a learning model for detecting the sightline), or may be processing that is executed by using a well-known sightline detection technique. For example, the sightline detection section 41 detects the user's pupils from the image that is acquired by the front camera 21, and detects the user's sightline based on the detected pupils. The user's sightline may be a sightline of the user's right eye, may be a sightline of the user's left eye, or may be a sightline that is derived based on the sightline of the user's right eye and the sightline of the user's left eye.

[Image Acquisition Section]

The image acquisition section 50 acquires the image (the image data) of the surrounding environment of the user. The image that is acquired by the image acquisition section 50 is transmitted to the estimation processing section 42. For example, the image acquisition section 50 acquires the image of the surrounding environment of the user by the following procedure.

Figure 9:
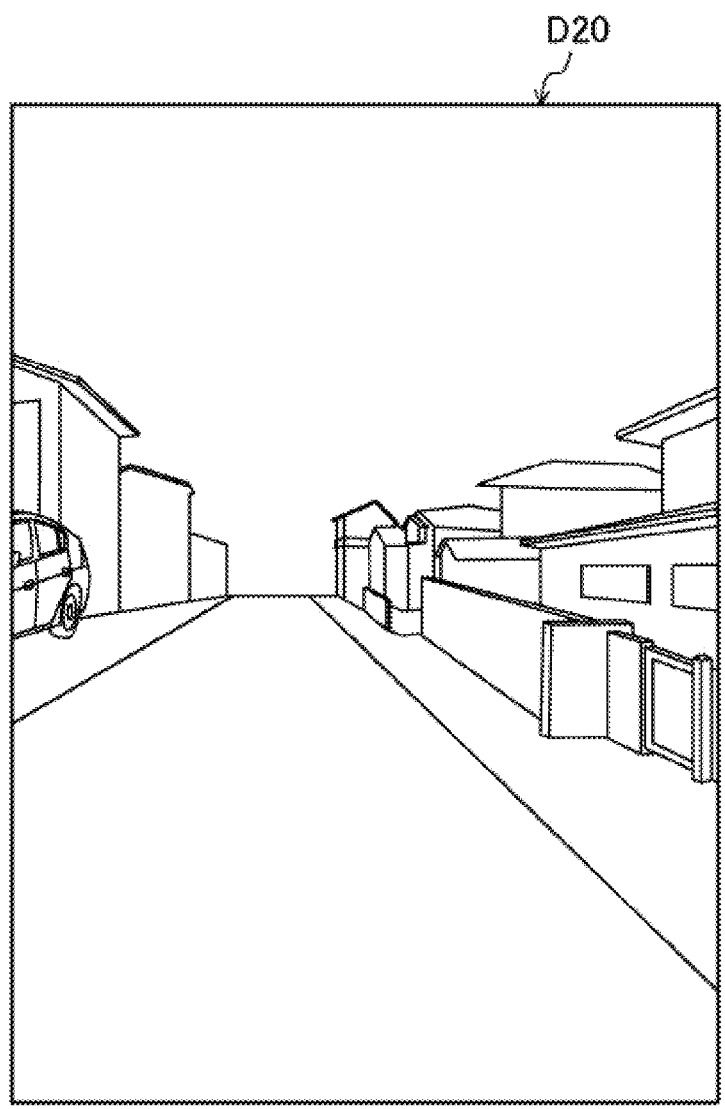
FIG. 9 is a view of a front environment image that shows environment in front of a user.
Figure 10:
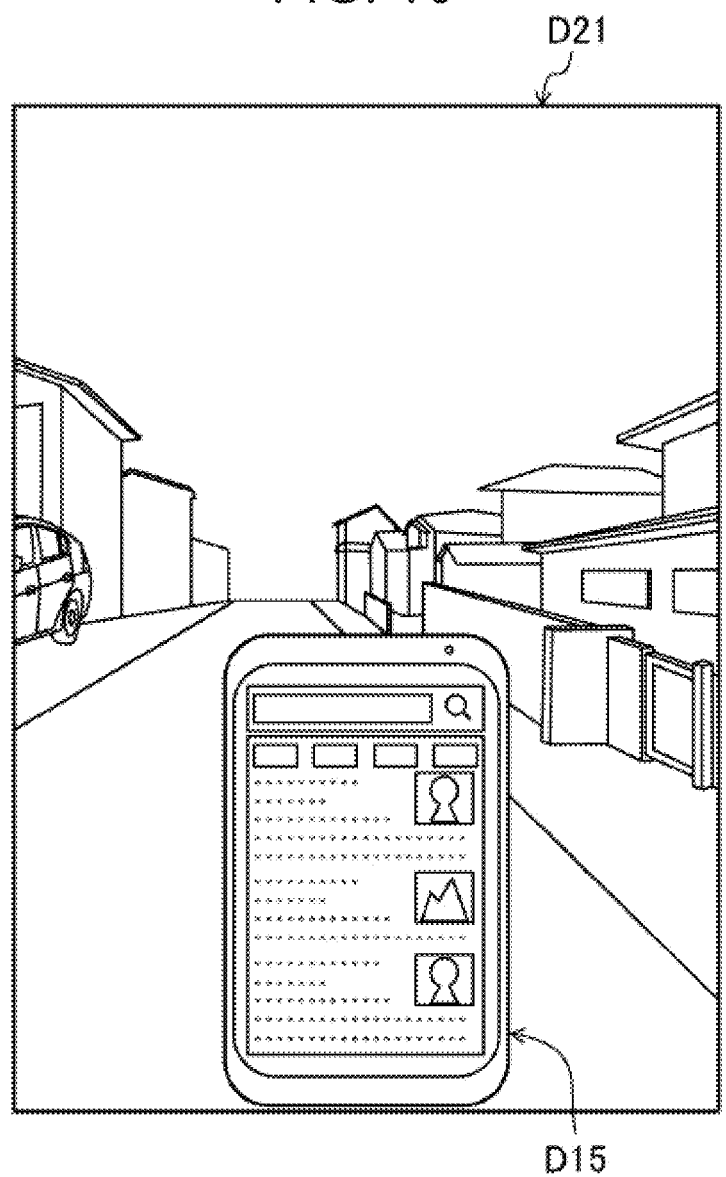
FIG. 10 is a view of the front environment image on which a mobile terminal image is superimposed.

First, the image acquisition section 50 acquires a front environment image D20 (see FIG. 9), which shows the front environment of the user, based on output of the rear camera 22. Next, the image acquisition section 50 synthesizes a mobile terminal image D15 (see FIG. 10), which shows the mobile terminal 10, with the front environment image D20, and thereby generates a front environment image D21 showing the front environment of the user. As illustrated in FIG. 10, in the front environment image D21, the mobile terminal image D15 is superimposed on the front environment image D20. The mobile terminal image D15 is generated by synthesizing an image, which is prepared in advance and shows the front surface of the mobile terminal 10, and the image displayed on the display section 11. In the mobile terminal image D15 illustrated in FIG. 10, the article browsing image D11 displayed on the display section 11 is superimposed on the image of the front surface of the mobile terminal 10.

The image acquisition section 50 may output the front environment image D20 showing the front environment of the user to the estimation processing section 42. The image acquisition section 50 may generate the image of the surrounding environment of the user based on the map information acquired by the communication section 24 and location information (the location of the mobile terminal 10) acquired by the location sensor 26.

[Main Task Detection Section]

The main task detection section 51 detects a main task of the user based on the information acquired by the information acquisition section 20. A detection result by the main task detection section 51 is transmitted to the estimation processing section 42. Examples of the main task of the user are the operation of the mobile terminal 10 corresponding to the operation task and walking corresponding to the walking task.

In this example, the main task detection section 51 detects that the main task of the user corresponds to the operation (the operation task) of the mobile terminal 10. For example, the main task detection section 51 detects the location of the mobile terminal 10 based on the output of the location sensor 26, and estimates a moving speed of the user based on a temporal change in the location of the mobile terminal 10. In addition, based on the output of the operation section 23, the main task detection section 51 detects that the user is operating the operation section 23. Then, in the case where the moving speed of the user falls below a predetermined first speed threshold and the operation by the user is given to the operation section 23 (the touch operation section), the main task detection section 51 outputs the detection result indicating that the main task of the user corresponds to the operation of the mobile terminal 10. The first speed threshold may be set to the maximum moving speed at which the user can be regarded as not walking but being stopped.

In this example, the main task detection section 51 detects that the main task of the user corresponds to walking (the walking task). For example, in the case where the moving speed of the user exceeds the first speed threshold but falls below a predetermined second speed threshold, the main task detection section 51 outputs the detection result indicating that the main task of the user corresponds to walking. The second speed threshold may be set to the maximum moving speed at which the user can be regarded as walking.

[Image Type Detection Section]

The image type detection section 52 detects a type of the image displayed on the display section 11 based on the information acquired by the information acquisition section 20. A detection result by the image type detection section 52 is transmitted to the estimation processing section 42. Examples of the type of the image are a type of the app related to the image and a category that is related to likeliness of occurrence of the user's bottom-up attention with respect to the image. The likeliness of the occurrence of the user's bottom-up attention with respect to the image depends on the high visibility proportion in the image (the proportion of the high visibility point in the image).

For example, the image type detection section 52 detects the likeliness of the occurrence of the user's bottom-up attention with respect to the image displayed on the display section 11. Then, the image type detection section 52 detects whether the image displayed on the display section 11 corresponds to the "high visibility image" and the "low visibility image" based on the likeliness of the occurrence of the user's bottom-up attention with respect to the image displayed on the display section 11.

More specifically, the image type detection section 52 detects the high visibility proportion in the image displayed on the display section 11. In the case where the high visibility proportion in the image displayed on the display section 11 exceeds the high visibility proportion threshold, the image type detection section 52 outputs the detection result indicating that the image displayed on the display section 11 corresponds to the "high visibility image". On the other hand, in the case where the high visibility proportion in the image displayed on the display section 11 does not exceed the high visibility proportion threshold, the image type detection section 52 outputs the detection result indicating that the image displayed on the display section 11 corresponds to the "low visibility image".

[Time Detection Section]

The time detection section 53 detects the cognitive response time of the user based on the information acquired by the information acquisition section 20. A detection result by the time detection section 53 is transmitted to the estimation processing section 42. For example, based on the sightline detected by the sightline detection section 41 and the image displayed on the display section 11, the time detection section 53 detects that the user has visually recognized the particular point (for example, the icon, the character on the dial, or the like) included in the image displayed on the display section 11. In addition, the time detection section 53 detects that the user gives an operation (more specifically, a touch) of selecting the point visually recognized by the user to the operation section 23. Then, the time detection section 53 detects, as the "cognitive response time", a time required from time at which the user visually recognizes the particular point included in the image displayed on the display section 11 to time at which the user gives the operation of selecting the particular point to the operation section 23.

[Erroneous Operation Detection Section]

The erroneous operation detection section 54 detects a frequency of the erroneous operation by the user based on the information acquired by the information acquisition section 20. A detection result by the erroneous operation detection section 54 is transmitted to the estimation processing section 42. Examples of the erroneous operation are a character input error and an icon selection error. For example, the erroneous operation detection section 54 determines adequacy of the character that is input by the user, detects a frequency of the character input error based on the determination result, and outputs the frequency of the character input error as the "frequency of the erroneous operation by the user". The detection of the erroneous operation may be processing that is executed by using a learning model generated by deep learning (a learning model for detecting the erroneous operation), or may be processing that is executed by using a well-known adequacy determination technique.

[Walking Pace Detection Section]

The walking pace detection section 55 detects a walking pace of the user based on the information acquired by the information acquisition section 20. A detection result by the walking pace detection section 55 is transmitted to the estimation processing section 42. For example, the walking pace detection section 55 detects the location of the mobile terminal 10 based on the output of the location sensor 26, estimates a variation in the moving speed of the user per unit time based on the temporal change in the location of the mobile terminal 10, and outputs the variation in the moving speed of the user per unit time as the "walking pace of the user".

[Wobbling Detection Section]

The wobbling detection section 56 detects wobbling (the tremor of the posture) of the user based on the information acquired by the information acquisition section 20. A detection result by the wobbling detection section 56 is transmitted to the estimation processing section 42. For example, the wobbling detection section 56 detects a width of a tremor of a posture of the mobile terminal 10 based on the output of the state sensor 27, estimates the width of the tremor of the posture of the user based on the width of the tremor of the posture of the mobile terminal 10, and outputs the width of the tremor of the posture of the user as the "wobbling of the user".

[Estimation Processing Section]

The estimation processing section 42 executes estimation processing for estimating the user state. In this example, the estimation processing section 42 executes first processing, second processing, third processing, fourth processing, fifth processing, and sixth processing based on the output of each of the sightline detection section 41, the image acquisition section 50, the main task detection section 51, the image type detection section 52, the time detection section 53, the erroneous operation detection section 54, the walking pace detection section 55, and the wobbling detection section 56. First estimation processing may include first to third processing and is based on an image displayed (when a user's main task is operating the mobile device 10). Second estimation processing may include fourth to sixth processing based on a surrounding environment (when a user's main task is walking).

The first processing is processing to estimate the user state based on the motion of the user's sightline with respect to the image displayed on the display section 11. The second processing is processing to estimate the user state based on the cognitive response time of the user. The third processing is processing to estimate the user state based on the frequency of the erroneous operation by the user. The fourth processing is processing to estimate the user state based on the motion of the user's sightline with respect to the surrounding environment of the user. The fifth processing is processing to estimate the user state based on the walking pace of the user. The sixth processing is processing to estimate the user state based on the wobbling of the user. A detailed description on the first to sixth processings will be made below.

In this example, the estimation processing section 42 includes a top-down measurement section 61, a bottom-up measurement section 62, and an estimation section 63.

<Top-Down Measurement Section>

In the first processing, the top-down measurement section 61 measures a first top-down index value TD1 that is correlated with the top-down attention source amount of the user with respect to the image displayed on the display section 11 based on the image displayed on the display section 11 and the user's sightline detected by the sightline detection section 41. In the fourth processing, the top-down measurement section 61 measures a second top-down index value TD2 that is correlated with the top-down attention source amount of the user with respect to the surrounding environment of the user based on the surrounding environment of the user and the user's sightline detected by the sightline detection section 41. As the top-down attention source amount of the user increases, the first top-down index value TD1 and the second top-down index value TD2 increase. In this example, the top-down measurement section 61 has a point of interest detection section 611 and a top-down index deriving section 612.

<<Point of Interest Detection Section>>

In the first processing, the point of interest detection section 611 detects the point of interest in the image displayed on the display section 11. In this example, the point of interest detection section 611 generates a point of interest map D30 (point of interest map data) that indicates the point of interest in the image displayed on the display section 11 based on the image (the image data) displayed on the display section 11. More specifically, in the case where the main task of the user detected by the main task detection section 51 corresponds to the operation (the operation task) of the mobile terminal 10, the point of interest detection section 611 receives the image (the image data) displayed on the display section 11. Then, the point of interest detection section 611 generates the point of interest map D30 as follows.

Figure 11:
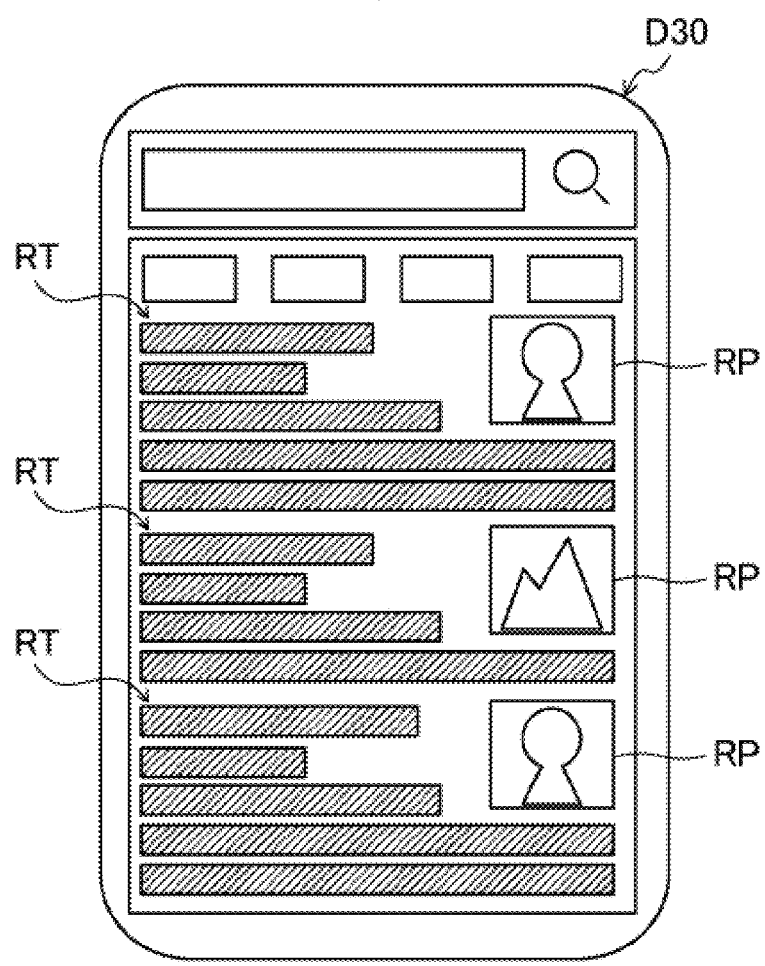
FIG. 11 is a view of a point of interest map that shows distribution of points of interest.

For example, the point of interest detection section 611 acquires the article browsing image D11 (see FIG. 4) that is displayed on the display section 11. Next, the point of interest detection section 611 detects the point of interest from the article browsing image D11. The detection of the point of interest may be processing that is executed by using a learning model generated by deep learning (a learning model for detecting the point of interest), or may be processing that is performed by using a well-known characteristic detection technique. Next, the point of interest detection section 611 generates the point of interest map D30 based on the detection result of the point of interest. As illustrated in FIG. 11, the point of interest map D30 indicates distribution of the points of interest in the image displayed on the display section 11. In an example illustrated in FIG. 11, hatched portions are the point of interest. More specifically, in the example illustrated in FIG. 11, the text area RT corresponds to the point of interest. Then, the point of interest detection section 611 generates the point of interest map D30 by the above procedure every time the image displayed on the display section 11 is updated (or in specified time intervals). In this way, the plural point of interest maps D30 that are arranged in a chronological order are acquired.

In the fourth processing, the point of interest detection section 611 detects the point of interest in the surrounding environment of the user. In this example, the point of interest detection section 611 generates a point of interest map (point of interest map data) that indicates the point of interest in the surrounding environment of the user based on the image (the image of the surrounding environment of the user) acquired by the image acquisition section 50. More specifically, in the case where the main task of the user detected by the main task detection section 51 corresponds to walking (the walking task), the point of interest detection section 611 receives the output of the image acquisition section 50. The point of interest map in the fourth processing is generated in a similar manner to the point of interest map D30 in the first processing.

<<Top-Down Index Deriving Section>>

In the first processing, the top-down index deriving section 612 derives the first top-down index value TD1 based on the motion of the user's sightline with respect to the point of interest in the image displayed on the display section 11. More specifically, in the first processing, the top-down index deriving section 612 derives the first top-down index value TD1 based on a matching degree (a matching frequency) between the point of interest in the image displayed on the display section 11 and the user's sightline. When the top-down attention source amount of the user increases, the matching degree between the point of interest in the image displayed on the display section 11 and the user's sightline increases, and the first top-down index value TD1 thereby increases.

In this example, in the first processing, the top-down index deriving section 612 derives, as the first top-down index value TD1, a value corresponding to the matching degree between the point of interest in the point of interest map D30 generated by the point of interest detection section 611 and the user's sightline detected by the sightline detection section 41. More specifically, the top-down index deriving section 612 executes the following processing for each predetermined measurement period.

First, the top-down index deriving section 612 extracts two or more of the point of interest maps D30 in the measurement period from the plural point of interest maps D30, which are arranged in the chronological order, and detects a focus point in each of the two or more of the point of interest maps D30 in the measurement period based on a direction of the user's sightline detected by the sightline detection section 41. The focus point is a point indicative of a position (coordinates) of the user's sightline in the point of interest map D30. For example, the top-down index deriving section 612 may detect, as the focus point, the position of the user's sightline from the point of interest map D30 at predetermined sampling intervals. Alternatively, the top-down index deriving section 612 may detect, as the focus point, the position of the user's sightline, a stagnation period of which is longer than a predetermined reference period.

Next, the top-down index deriving section 612 determines whether the focus point, which is detected from the point of interest map D30 in the measurement period, matches the point of interest indicated in the point of interest map D30.

Then, the top-down index deriving section 612 derives the first top-down index value TD1 based on a result of the matching determination between the focus point and the point of interest. For example, the first top-down index value TD1 is a value that corresponds to a ratio of the number of the focus points matching the points of interest to the total number of the focus points in the measurement period (hereinafter described as an "interest matching ratio"). This interest matching ratio is an example of the matching degree between the points of interest and the user's sightline. In this way, the first top-down index value TD1 is derived for each measurement period.

In the fourth processing, the top-down index deriving section 612 derives the second top-down index value TD2 based on the motion of the user's sightline with respect to the point of interest in the surrounding environment of the user. More specifically, in the fourth processing, the top-down index deriving section 612 derives the second top-down index value TD2 based on a matching degree (a matching frequency) between the point of interest in the surrounding environment of the user and the user's sightline. When the top-down attention source amount of the user is increased, the matching degree between the point of interest in the surrounding environment of the user and the user's sightline is increased, and the second top-down index value TD2 is thereby increased.

In this example, in the fourth processing, the top-down index deriving section 612 derives, as the second top-down index value TD2, a value corresponding to the matching degree between the point of interest indicated in the point of interest map generated by the point of interest detection section 611 and the user's sightline detected by the sightline detection section 41. The second top-down index value TD2 in the fourth processing is derived in a similar manner to the first top-down index value TD1 in the first processing.

<Bottom-Up Measurement Section>

In the first processing, the bottom-up measurement section 62 measures a first bottom-up index value BU1 that is correlated with the bottom-up attention source amount of the user with respect to the image displayed on the display section 11 based on the image displayed on the display section 11 and the user's sightline detected by the sightline detection section 41. In the fourth processing, the bottom-up measurement section 62 measures a second bottom-up index value BU2 that is correlated with the bottom-up attention source amount of the user with respect to the surrounding environment of the user based on the surrounding environment of the user and the user's sightline detected by the sightline detection section 41. As the bottom-up attention source amount of the user increases, the first bottom-up index value BU1 and the second bottom-up index value BU2 increase. In this example, the bottom-up measurement section 62 has a saliency detection section 621 and a bottom-up index deriving section 622.

<<Saliency Detection Section>>

In the first processing, the saliency detection section 621 detects distribution of the saliency in the image displayed on the display section 11. In this example, the saliency detection section 621 generates a saliency map D40 (saliency map data, see FIG. 12) that shows the distribution of the saliency in the image displayed on the display section 11 based on the image (the image data) displayed on the display section 11. More specifically, in the case where the main task of the user detected by the main task detection section 51 corresponds to the operation (the operation task) of the mobile terminal 10, the saliency detection section 621 receives the image (the image data) displayed on the display section 11, e.g., in the picture areas RP. Then, the saliency detection section 621 generates the saliency map D40 by the following procedure.

For example, similar to the point of interest detection section 611, the saliency detection section 621 acquires the article browsing image D11 (see FIG. 4) that is displayed on the display section 11. Next, the saliency detection section 621 generates the saliency map D40 by executing saliency map generation processing on the article browsing image D11. A well-known technique such as saliency detection can be used for the saliency map generation processing. For example, the saliency detection section 621 generates a saliency map for each of the characteristics such as the color, the luminance, the direction, and the motion, and adds the saliency maps of those image characteristics. In this way, the saliency detection section 621 generates a final saliency map (a saliency map to which all the image characteristics are reflected).

Figure 12:
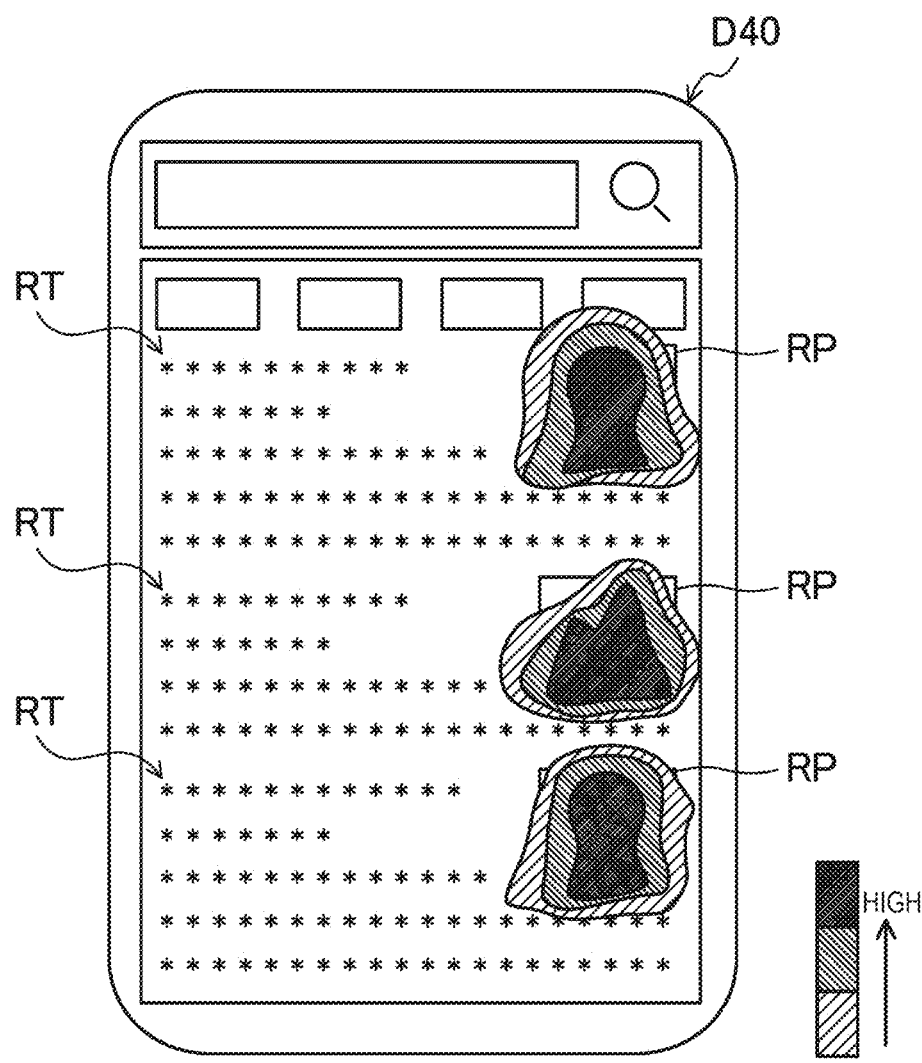
FIG. 12 is a view of a saliency map that shows distribution of saliency.

As illustrated in FIG. 12, the saliency map D40 shows the distribution of the saliency in the image displayed on the display section 11. Values of pixels in the saliency map D40 each represent the saliency in an area of the respective pixel. In an example illustrated in FIG. 12, a degree of the saliency is indicated by density of hatching. As the density of hatching increases, the saliency in a hatched area increases.

Then, the saliency detection section 621 generates the saliency map D40 by the above procedure every time the image displayed on the display section 11 is updated (or in the specified time intervals). In this way, the plural saliency maps D40 that are arranged in the chronological order are acquired.

In the fourth processing, the saliency detection section 621 detects distribution of the saliency in the surrounding environment of the user. In this example, the saliency detection section 621 generates a saliency map (saliency map data) that indicates the distribution of the saliency in the surrounding environment of the user based on the image (the image of the surrounding environment of the user) acquired by the image acquisition section 50. More specifically, in the case where the main task of the user detected by the main task detection section 51 corresponds to walking (the walking task), the saliency detection section 621 receives the output of the image acquisition section 50. The saliency map in the fourth processing is generated in a similar manner to the saliency map D40 in the first processing.

<<Bottom-Up Index Deriving Section>>

In the first processing, the bottom-up index deriving section 622 derives the first bottom-up index value BU1 based on the motion of the user's sightline with respect to the distribution of the saliency in the image displayed on the display section 11. More specifically, in the first processing, the bottom-up index deriving section 622 derives the first bottom-up index value BU1 based on a matching degree (a matching frequency) between the high visibility point in the image displayed on the display section 11 and the user's sightline. When the bottom-up attention source amount of the user increases, the matching degree between the high visibility point in the image displayed on the display section 11 and the user's sightline increases, and the first bottom-up index value BU1 thereby increases.

In this example, in the first processing, the bottom-up index deriving section 622 derives, as the first bottom-up index value BU1, a value corresponding to the matching degree between the high visibility point in saliency map D40 generated by the saliency detection section 621 and the user's sightline detected by the sightline detection section 41. More specifically, the bottom-up index deriving section 622 executes the following first derivation processing, second derivation processing, third derivation processing, and fourth derivation processing for each predetermined calculation period.

In the first derivation processing, the bottom-up index deriving section 622 extracts the two or more saliency maps D40 in the calculation period from plural saliency maps D40 that are arranged in the chronological order. Then, based on the direction of the user's sightline detected by the sightline detection section 41, the bottom-up index deriving section 622 detects the focus point in each of the two or more saliency maps D40 in the measurement period, and detects the saliency at the focus point. The focus point is a point indicative of the position (the coordinates) of the user's sightline in the saliency map D40. For example, the bottom-up index deriving section 622 may detect, as the focus point, the position of the user's sightline from the saliency map D40 at predetermined sampling intervals. Alternatively, the bottom-up index deriving section 622 may detect, as the focus point, the position of the user's sightline, the stagnation period of which is longer than the predetermined reference period. In this first derivation processing, the saliency at the focus point per specified time can be acquired. As illustrated in FIG. 13, the saliency at the focus point varies over time.

In the second derivation processing, the bottom-up index deriving section 622 extracts the two or more saliency maps D40 in the calculation period from the plural saliency maps D40 that are arranged in the chronological order. Then, the bottom-up index deriving section 622 designates a random point in each of the two or more saliency maps D40 in the measurement period, and detects the saliency at the random point. The random point is a point indicative of a position, which is designated randomly, in the saliency map D40. The random point may be designated in the saliency map D40, in which the focus point is detected by the first derivation processing, among the plural saliency maps D40. That is, time at which the saliency at the random point is detected may match the time at which the saliency at the focus point is detected. In this second derivation processing, the saliency at the random point per specified time can be acquired. As illustrated in FIG. 14, the saliency at the random point varies over time.

Next, the third derivation processing is executed. In the third derivation processing, the bottom-up index deriving section 622 derives receiver operating characteristic (ROC) curve indicative of a relationship between a "probability that the saliency at the focus point exceeds a threshold" and a "probability that the saliency at the random point exceeds the threshold" based on the saliency at the focus point per specified time in the calculation period, which is acquired by the first derivation processing, and the saliency at the random point per specified time in the calculation period, which is acquired by the second derivation processing.

More specifically, the bottom-up index deriving section 622 changes the threshold related to the saliency stepwise from a maximum value to a minimum value. In addition, the top-down index deriving section 612 executes the following processing every time the threshold is changed.

First, the bottom-up index deriving section 622 calculates the number of the saliency at the focus point that exceeds the threshold among the saliency at the focus point per specified time in the calculation period. Then, the bottom-up index deriving section 622 divides the number of the saliency at the focus points that exceeds the threshold by the total number of the saliency at the focus points in the calculation period. In this way, the bottom-up index deriving section 622 calculates the probability that the saliency at the focus point exceeds the threshold. In addition, the bottom-up index deriving section 622 calculates the number of the saliency at the random point that exceeds the threshold among the saliency at the random point per specified time in the calculation period. Then, the bottom-up index deriving section 622 divides the number of the saliency at the random points that exceeds the threshold by the total number of the saliency at the random points in the calculation period. In this way, the bottom-up index deriving section 622 calculates the probability that the saliency at the random point exceeds the threshold.

Figure 15:
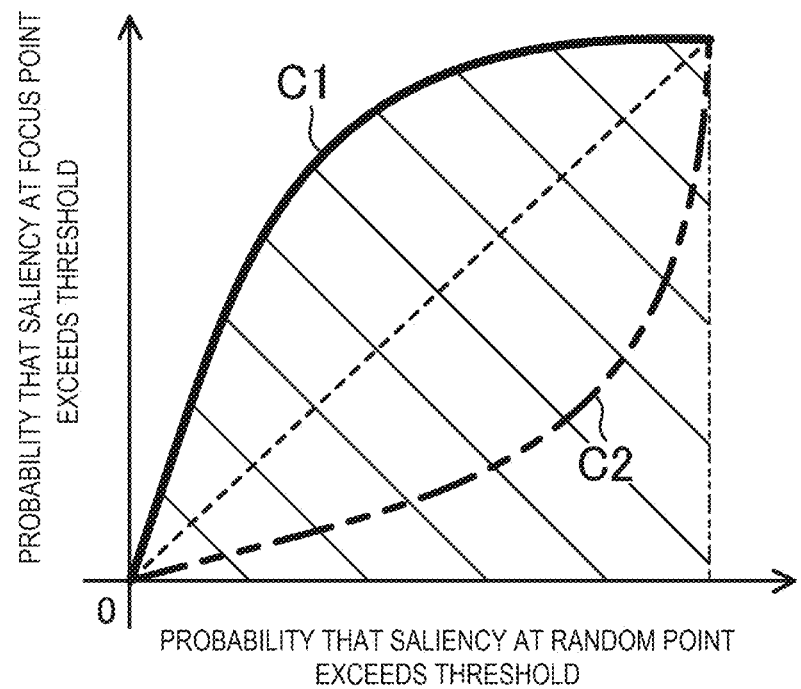
FIG. 15 is a graph illustrating a relationship between a probability that the saliency at the focus point exceeds a threshold and a probability that the saliency at the random point exceeds the threshold.

Then, the bottom-up index deriving section 622 derives the ROC curve based on a combination of the "probability that the saliency at the focus point exceeds the threshold" and the "probability that the saliency at the random point exceeds the threshold" calculated per threshold. FIG. 15 illustrates the ROC curve. This ROC curve varies according to intensification of a tendency that the user's sightline is attracted to the high visibility point. For example, in the case where the user's sightline tends to be pointed at the high visibility point, as indicated by a first curve C1 in FIG. 15, the ROC curve is an upwardly projected curve in comparison with a linear line (a linear line indicated by a broken line) with a gradient of one. Meanwhile, in the case where the user's sightline tends to be pointed at the low visibility point, as indicated by a second curve C2 in FIG. 15, the ROC curve is a downwardly projected curve in comparison with the linear line with the gradient of one.

In the fourth derivation processing, the bottom-up index deriving section 622 calculates, as a saliency index value, an area under the curve (AUC) value that corresponds to an area under the ROC curve. For example, in the case where the first curve C1 in FIG. 15 is the ROC curve, the AUC value corresponds to an area of the hatched region in FIG. 15. For example, as the tendency of the user's sightline to be pointed at the high visibility point is intensified, the AUC value as the saliency index value is increased. Meanwhile, as the tendency of the user's sightline to be pointed at the low visibility point is intensified, the AUC value as the saliency index value is reduced. In this way, the saliency index value is derived for each calculation period.

Furthermore, the bottom-up index deriving section 622 executes fifth derivation processing for each predetermined measurement period. The measurement period is longer than the calculation period. The plural calculation periods are included in each of the measurement periods. In the fifth derivation processing, the bottom-up index deriving section 622 determines whether the saliency index value in the measurement period exceeds a predetermined high visibility threshold. Then, the bottom-up index deriving section 622 derives the first bottom-up index value BU1 based on a determination result of the saliency index value. For example, the first bottom-up index value BU1 is a value that corresponds to a ratio of the number of the saliency index values exceeding the high visibility threshold to the total number of the saliency index values in the measurement period (hereinafter described as a "high index ratio"). This high index ratio is an example of the matching degree between the high visibility point and the user's sightline. In this way, the first bottom-up index value BU1 is derived for each measurement period.

In the fourth processing, the bottom-up index deriving section 622 derives the second bottom-up index value BU2 based on the motion of the user's sightline with respect to the distribution of the saliency in the surrounding environment of the user. More specifically, in the fourth processing, the bottom-up index deriving section 622 derives the second bottom-up index value BU2 based on a matching degree (a matching frequency) between the high visibility point in the surrounding environment of the user and the user's sightline. When the bottom-up attention source amount of the user is increased, the matching degree between the high visibility point in the surrounding environment of the user and the user's sightline is increased, and the second bottom-up index value BU2 is thereby increased.

In this example, in the fourth processing, the bottom-up index deriving section 622 derives, as the second bottom-up index value BU2, a value corresponding to the matching degree between the high visibility point in saliency map, which is generated by the saliency detection section 621, and the user's sightline detected by the sightline detection section 41. The second bottom-up index value BU2 in the fourth processing is derived in a similar manner to the first bottom-up index value BU1 in the first processing.

<Estimation Section>

In the first processing, the estimation section 63 estimates the user state based on the first top-down index value TD1 and the first bottom-up index value BU1. More specifically, in the first processing, the estimation section 63 estimates the user state based on the change in the first top-down index value TD1 and the change in the first bottom-up index value BU1. In the fourth processing, the estimation section 63 estimates the user state based on the second top-down index value TD2 and the second bottom-up index value BU2. More specifically, in the fourth processing, the estimation section 63 estimates the user state based on the change in the second top-down index value TD2 and the change in the second bottom-up index value BU2. A detailed description on the estimation of the user state will be made below.

[Operation of Estimation Processing Section]

Figure 16:
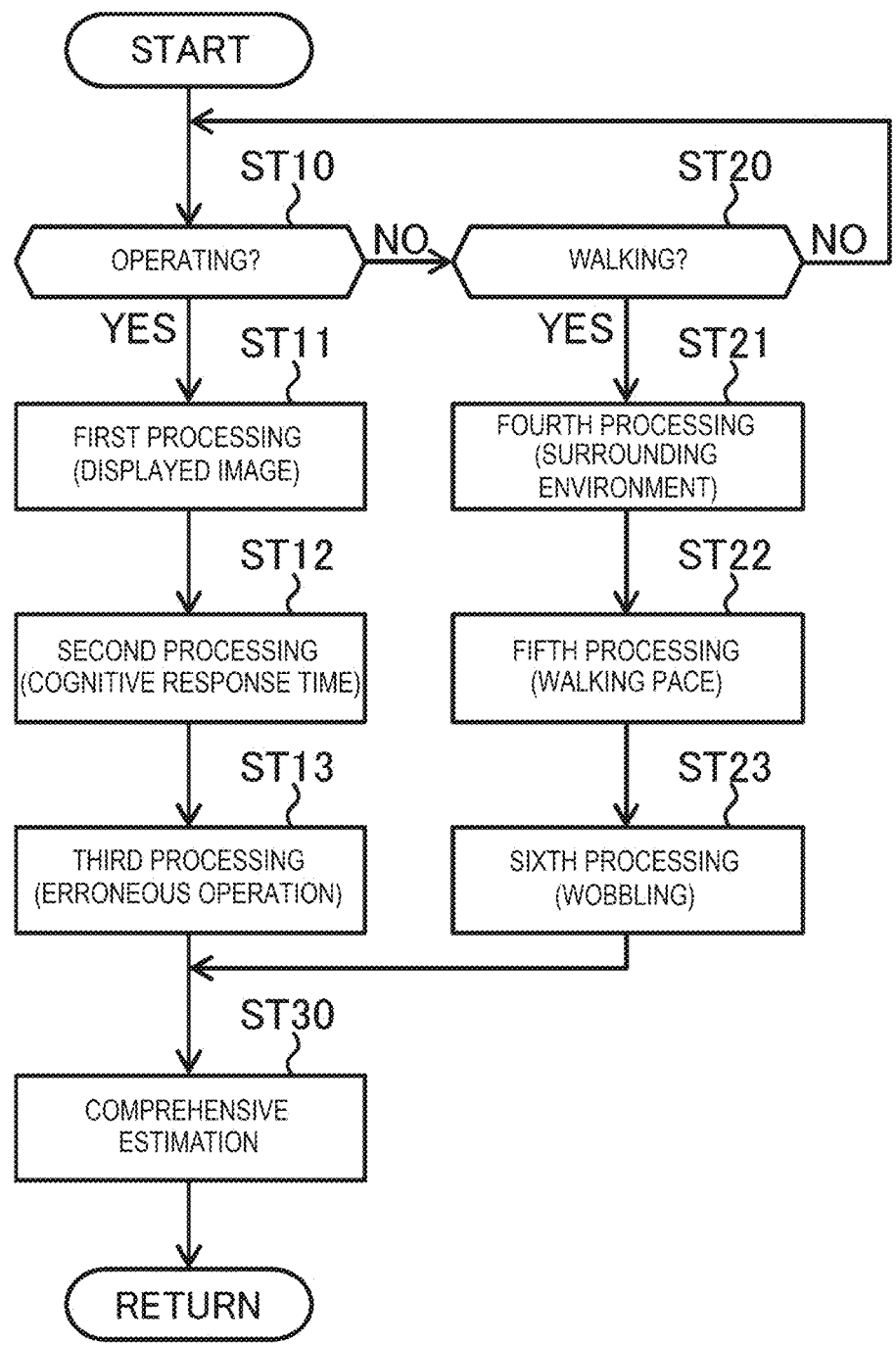
FIG. 16 is a flowchart for illustrating operation of the estimation processing section.

Next, a description will be made on the operation of the estimation processing section 42 with reference to FIG. 16. In this example, the estimation processing section 42 selectively executes a group of the first processing, the second processing, and the third processing or a group of the fourth processing, the fifth processing, and the sixth processing according to the main task of the user. More specifically, the estimation processing section 42 executes the first processing, the second processing, and the third processing in the case where the main task of the user corresponds to the operation of the mobile terminal 10. Meanwhile, the estimation processing section 42 executes the fourth processing, the fifth processing, and the sixth processing in the case where the main task of the user corresponds to walking. For example, the estimation processing section 42 executes the following processing at predetermined estimation intervals (for example, every 10 minutes).

<Step ST10>

The estimation section 63 determines whether the main task of the user corresponds to the operation (the operation task) of the mobile terminal 10 based on the detection result by the main task detection section 51. If the main task of the user corresponds to the operation of the mobile terminal 10, processing in steps ST11 to ST13 is executed. If not, processing in step ST20 is executed.

<Steps ST11 to ST13>

In the case where the main task of the user corresponds to the operation of the mobile terminal 10, the estimation section 63 executes the first processing (step ST11), the second processing (step ST12), and the third processing (step ST13). When such processing is completed, processing in step ST30 is executed.

<Step ST20>

In the case where the main task of the user does not correspond to the operation of the mobile terminal 10, the estimation section 63 determines whether the main task of the user corresponds to walking (the walking task) based on the detection result by the main task detection section 51. If the main task of the user corresponds to walking, processing in steps ST21 to ST23 is executed. If not, the processing in step ST10 is executed.

<Steps ST21 to ST23>

In the case where the main task of the user corresponds to walking, the estimation section 63 executes the fourth processing (step ST21), the fifth processing (step ST22), and the sixth processing (step ST23). When such processing is completed, the processing in step ST30 is executed.

<Step ST30>

When the processing in steps ST11 to ST13 (or the processing in steps ST21 to ST23) is completed, the estimation section 63 comprehensively estimates the user state based on the estimation result related to the user state, which is acquired from the processing in steps ST11 to ST13 (or the processing in steps ST21 to ST23). A detailed description on the processing in step ST30 (comprehensive estimation) will be made below.

[First Processing]

Figure 17:
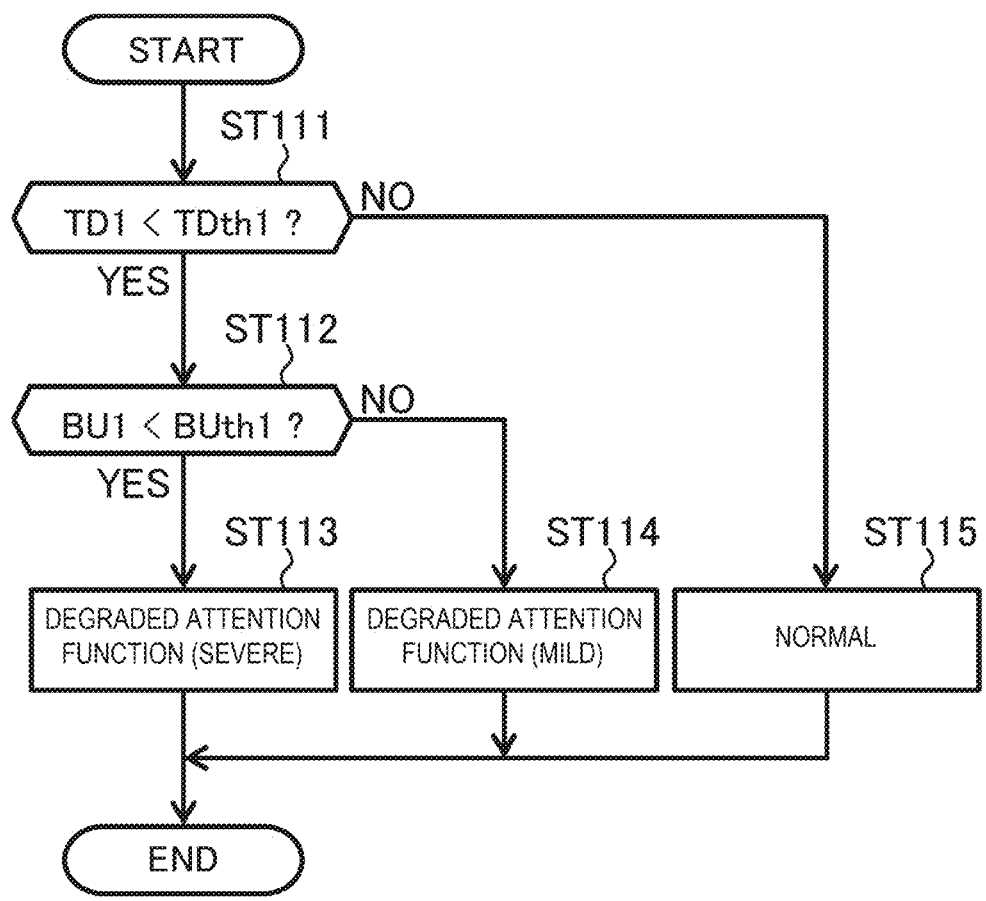
FIG. 17 is a flowchart for illustrating first processing.

Next, a description will be made on the first processing that is the processing in step ST11 with reference to FIG. 17. As described above, the first processing estimates the user state based on the motion of the user's sightline with respect to the image displayed on the display section 11. In the following first processing, the first attention function degraded state and the second attention function degraded state may be distinguished from each other.

<Step ST111>

The estimation section 63 determines whether the first top-down index value TD1 falls below a predetermined first top-down threshold TDth1. For example, the first top-down threshold TDth1 is set to a value that corresponds to the top-down attention demand amount of the user in a case where the main task of the user corresponds to the operation of the mobile terminal 10. If the first top-down index value TD1 falls below the first top-down threshold TDth1, processing in step ST112 is executed. If not, processing in step ST115 is executed.

<Step ST112>

The estimation section 63 determines whether the first bottom-up index value BU1 falls below a predetermined first bottom-up threshold BUth1. For example, the first bottom-up threshold BUth1 is set to a value that corresponds to the bottom-up attention demand amount of the user in the case where the main task of the user corresponds to the operation of the mobile terminal 10. If the first bottom-up index value BU1 falls below the first bottom-up threshold BUth1, processing in step ST113 is executed. If not, processing in step ST114 is executed.

<Step ST113>

In the case where the first top-down index value TD1 falls below the first top-down threshold TDth1, and the first bottom-up index value BU1 falls below the first bottom-up threshold BUth1, the estimation section 63 estimates that the user state is the second attention function degraded state (severe degradation of the attention function). In this example, the estimation section 63 turns on a flag indicative of the second attention function degraded state.

<Step ST114>

In the case where the first top-down index value TD1 falls below the first top-down threshold TDth1, and the first bottom-up index value BU1 does not fall below the first bottom-up threshold BUth1, the estimation section 63 does not estimate that the user state is the second attention function degraded state, but estimates that the user state is the first attention function degraded state (mild degradation of the attention function). In this example, the estimation section 63 turns on a flag indicative of the first attention function degraded state.

<Step ST115>

In the case where the first top-down index value TD1 does not fall below the first top-down threshold TDth1, the estimation section 63 does not estimate that the user state is the attention function degraded state, but estimates that the user state is the normal state. In this example, the estimation section 63 does not turn on the flag indicative of the attention function degraded state.

[Second Processing]

Figure 18:
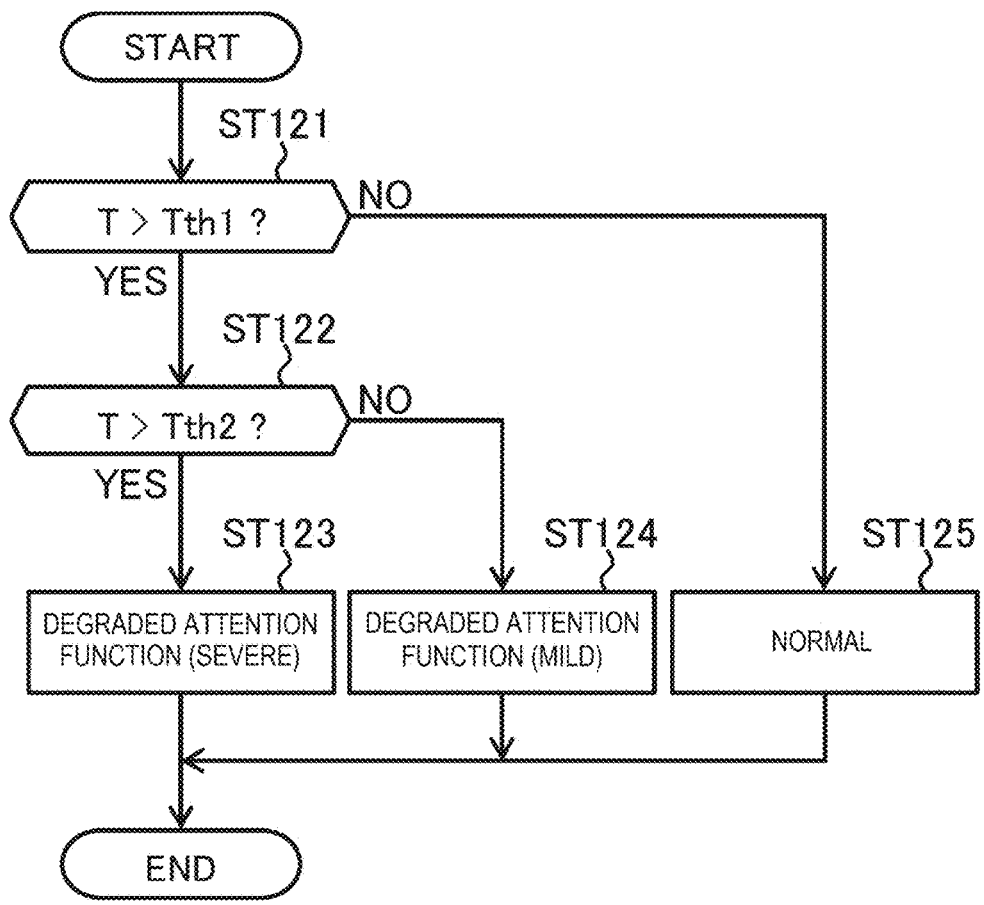
FIG. 18 is a flowchart for illustrating second processing.

Next, a description will be made on the second processing that is the processing in step ST12 with reference to FIG. 18. As described above, the second processing estimates the user state based on the cognitive response time of the user. In the following second processing, the first attention function degraded state and the second attention function degraded state may be distinguished from each other.

<Step ST121>

The estimation section 63 determines whether a cognitive response time T exceeds a predetermined first time threshold Tth1. If the cognitive response time T exceeds the first time threshold Tth1, processing in step ST122 is executed. If not, processing in step ST125 is executed.

<Step ST122>

The estimation section 63 determines whether the cognitive response time T exceeds a predetermined second time threshold Tth2. The second time threshold Tth2 is longer than the first time threshold Tth1. If the cognitive response time T falls below the second time threshold Tth2, processing in step ST123 is executed. If not, processing in step ST124 is executed.

<Step ST123>

If the cognitive response time T exceeds the second time threshold Tth2, the estimation section 63 estimates that the user state is the second attention function degraded state (the severe degradation of the attention function). In this example, the estimation section 63 turns on the flag indicative of the second attention function degraded state.

<Step ST124>

In the case where the cognitive response time T exceeds the first time threshold Tth1 but does not exceed the second time threshold Tth2, the estimation section 63 does not estimate that the user state is the second attention function degraded state, but estimates that the user state is the first attention function degraded state (the mild degradation of the attention function). In this example, the estimation section 63 turns on the flag indicative of the first attention function degraded state.

<Step ST125>

In the case where the cognitive response time T does not exceed the first time threshold Tth1, the estimation section 63 does not estimate that the user state is the attention function degraded state, but estimates that the user state is the normal state. In this example, the estimation section 63 does not turn on the flag indicative of the attention function degraded state.

[Third Processing]

Figure 19:
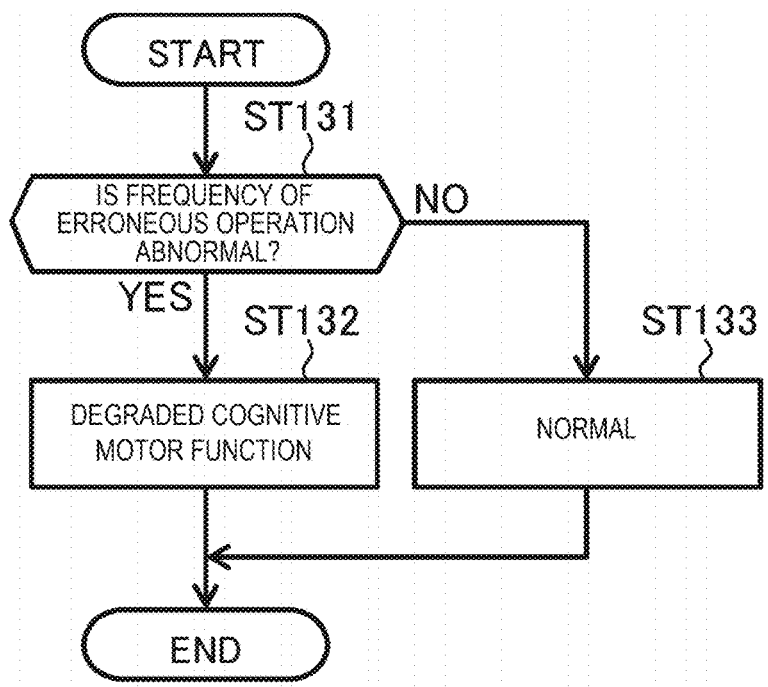
FIG. 19 is a flowchart for illustrating third processing.

Next, a description will be made on the third processing that is the processing in step ST13 with reference to FIG. 19. As described above, the third processing is the processing to estimate the user state based on the frequency of the erroneous operation by the user.

<Step ST131>

The estimation section 63 determines whether the frequency of the erroneous operation by the user in a specified time is abnormal. For example, in the case where the frequency of the erroneous operation by the user in the specified time exceeds a predetermined allowable frequency, the estimation section 63 determines that the frequency of the erroneous operation by the user in the specified time is abnormal. If the frequency of the erroneous operation by the user in the specified time is abnormal, the processing proceeds to step ST132. If not, the processing proceeds to step ST133.

<Step ST132>

In the case where the frequency of the erroneous operation by the user in the specified time is abnormal, the estimation section 63 estimates that the user state is the cognitive motor function degraded state. In this example, the estimation section 63 turns on a flag indicative of the cognitive motor function degraded state.

<Step ST133>

In the case where the frequency of the erroneous operation by the user in the specified time is not abnormal, the estimation section 63 does not estimate that the user state is the cognitive motor function degraded state, but estimates that the user state is the normal state. In this example, the estimation section 63 does not turn on the flag indicative of the cognitive motor function degraded state.

[Fourth Processing]

Figure 20:
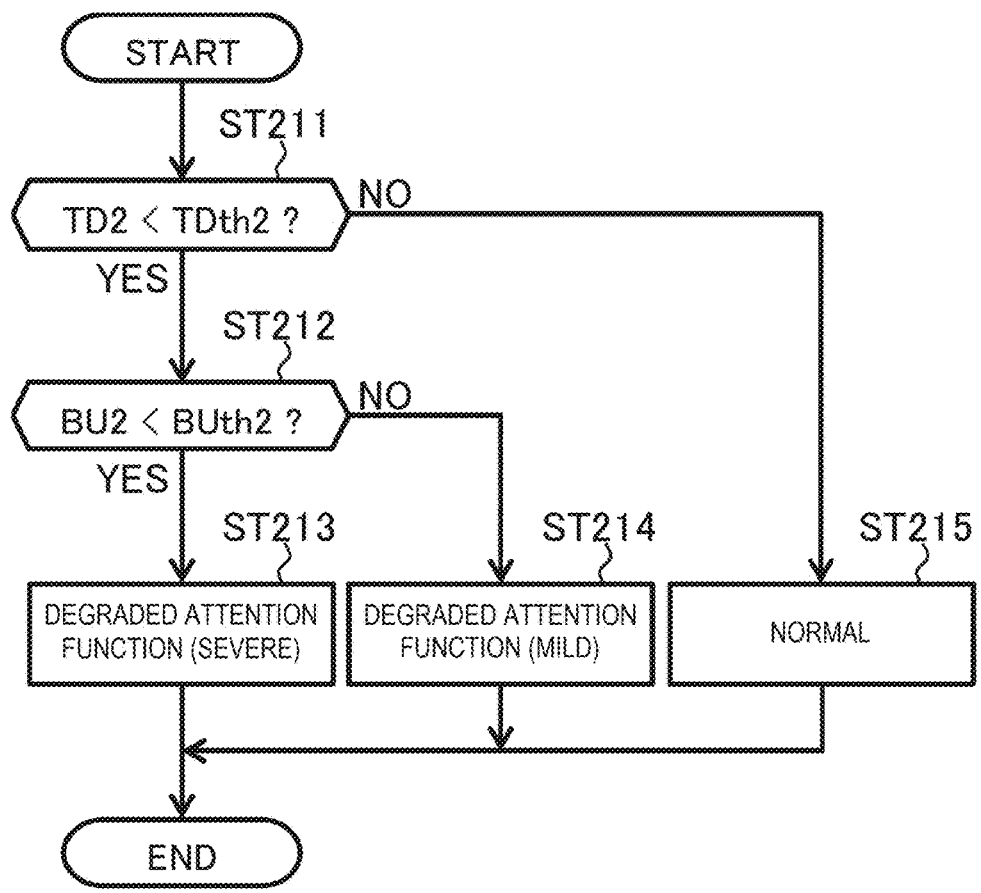
FIG. 20 is a flowchart for illustrating fourth processing.

Next, a description will be made on the fourth processing that is the processing in step ST21 with reference to FIG. 20. As described above, the fourth processing is the processing to estimate the user state based on the motion of the user's sightline with respect to the surrounding environment of the user. In the following fourth processing, the first attention function degraded state and the second attention function degraded state may be distinguished from each other.

<Step ST211>

The estimation section 63 determines whether the second top-down index value TD2 falls below a predetermined second top-down threshold TDth2. For example, the second top-down threshold TDth2 is set to a value that corresponds to the top-down attention demand amount of the user in the case where the main task of the user corresponds to walking. If the second top-down index value TD2 falls below the second top-down threshold TDth2, processing in step ST212 is executed. If not, processing in step ST215 is executed.

<Step ST212>

The estimation section 63 determines whether the second bottom-up index value BU2 falls below a predetermined second bottom-up threshold BUth2. For example, the second bottom-up threshold BUth2 is set to a value that corresponds to the bottom-up attention demand amount of the user in the case where the main task of the user corresponds to walking. If the second bottom-up index value BU2 falls below the second bottom-up threshold BUth2, processing in step ST213 is executed. If not, processing in step ST214 is executed.

<Step ST213>

In the case where the second top-down index value TD2 falls below the second top-down threshold TDth2, and the second bottom-up index value BU2 falls below the second bottom-up threshold BUth2, the estimation section 63 estimates that the user state is the second attention function degraded state (the severe degradation of the attention function). In this example, the estimation section 63 turns on the flag indicative of the second attention function degraded state.

<Step ST214>

In the case where the second top-down index value TD2 falls below the second top-down threshold TDth2, and the second bottom-up index value BU2 does not fall below the second bottom-up threshold BUth2, the estimation section 63 does not estimate that the user state is the second attention function degraded state, but estimates that the user state is the first attention function degraded state (the mild degradation of the attention function). In this example, the estimation section 63 turns on the flag indicative of the first attention function degraded state.

<Step ST215>

In the case where the second top-down index value TD2 does not fall below the second top-down threshold TDth2, the estimation section 63 does not estimate that the user state is the attention function degraded state, but estimates that the user state is the normal state. In this example, the estimation section 63 does not turn on the flag indicative of the attention function degraded state.

[Fifth Processing]

Figure 21:
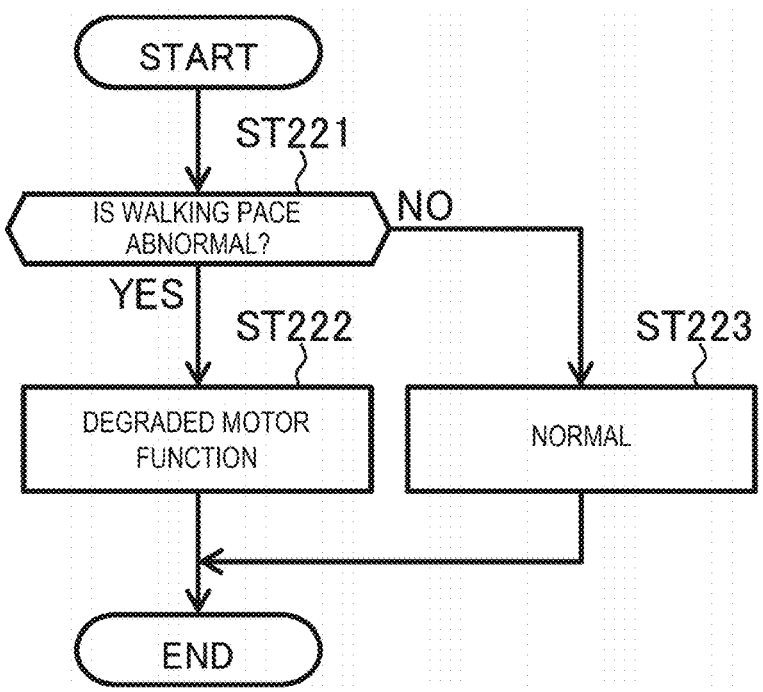
FIG. 21 is a flowchart for illustrating fifth processing.

Next, a description will be made on the fifth processing that is the processing in step ST22 with reference to FIG. 21. As described above, the fifth processing is the processing to estimate the user state based on the walking pace of the user.

<Step ST221>

The estimation section 63 determines whether the walking pace of the user in a specified time is abnormal. For example, the estimation section 63 measures duration of a state where the variation in the moving speed of the user per unit time exceeds a predetermined allowable amount. Then, in the case where the duration exceeds a predetermined allowable time, the estimation section 63 determines that the walking pace of the user in the specified time is abnormal. If the walking pace of the user in the specified time is abnormal, the processing proceeds to step ST222. If not, the processing proceeds to step ST223.

<Step ST222>

In the case where the walking pace of the user in the specified time is abnormal, the estimation section 63 estimates that the user state is the motor function degraded state. In this example, the estimation section 63 turns on the flag indicative of the motor function degraded state.

<Step ST223>

In the case where the walking pace of the user in the specified time is not abnormal, the estimation section 63 does not estimate that the user state is the motor function degraded state, but estimates that the user state is the normal state. In this example, the estimation section 63 does not turn on the flag indicative of the motor function degraded state.

[Sixth Processing]

Figure 22:
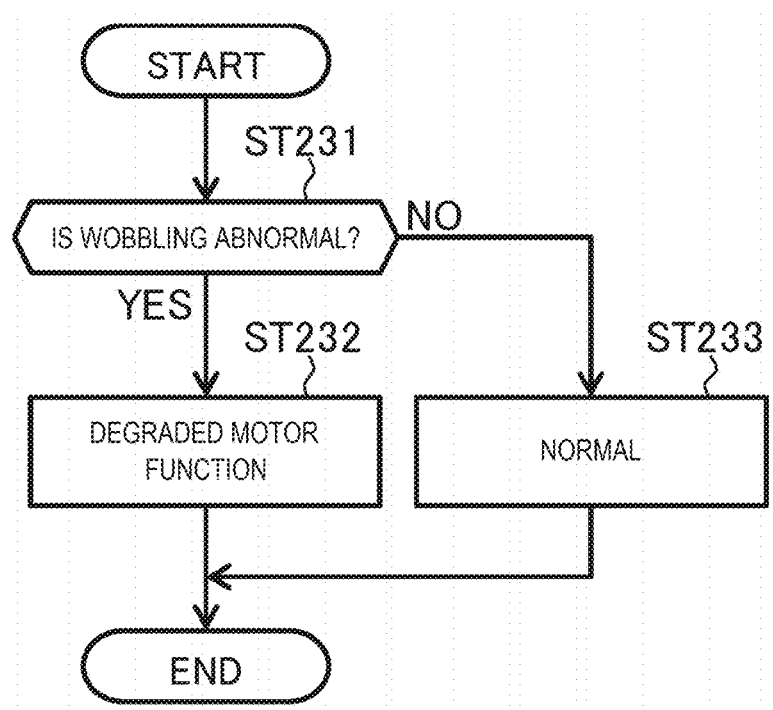
FIG. 22 is a flowchart for illustrating sixth processing.

Next, a description will be made on the sixth processing that is the processing in step ST23 with reference to FIG. 22. As described above, the sixth processing estimates the user state based on wobbling of the user.

<Step ST231>

The estimation section 63 determines whether wobbling of the user in a specified time is abnormal. For example, the estimation section 63 measures duration of a state where the wobbling width of the posture of the user exceeds a predetermined allowable width. Then, in the case where the duration exceeds a predetermined allowable time, the estimation section 63 determines that wobbling of the user in the specified time is abnormal. If wobbling of the user in the specified time is abnormal, the processing proceeds to step ST232. If not, the processing proceeds to step ST233.

<Step ST232>

In the case where wobbling of the user in the specified time is abnormal, the estimation section 63 estimates that the user state is the motor function degraded state. In this example, the estimation section 63 turns on the flag indicative of the motor function degraded state.

<Step ST233>

In the case where wobbling of the user in the specified time is not abnormal, the estimation section 63 does not estimate that the user state is the motor function degraded state, but estimates that the user state is the normal state. In this example, the estimation section 63 does not turn on the flag indicative of the motor function degraded state.

[Comprehensive Evaluation]

Next, a description will be made on the comprehensive evaluation that is the processing in step ST30. The estimation section 63 comprehensively estimates the user state based on the results of the first to sixth processings. For example, the estimation section 63 may be configured to perform the following operation.

The estimation section 63 may output all the results of the first to third processings (or the fourth to sixth processings) as the estimation result. For example, in the case where the estimation section 63 turns on the flag indicative of the first attention function degraded state in the first processing, and turns on the flag indicative of the cognitive motor function degraded state in the third processing, the estimation section 63 outputs such an estimation result that the user state is the first attention function degraded state and the cognitive motor function degraded state. In this example, the estimation section 63 turns on both the flag indicative of the first attention function degraded state and the flag indicative of the cognitive motor function degraded state.

Alternatively, in regard to the results of the first to third processings (or the fourth to sixth processings), the estimation section 63 may make a majority decision, and may output a result of the majority decision as the estimation result. For example, in the case where the estimation section 63 turns on the flag indicative of the first attention function degraded state in each of the first processing and the second processing, and turns on the flag indicative of the cognitive motor function degraded state in the third processing, the estimation section 63 outputs such an estimation result that the user state is the first attention function degraded state. In this example, the estimation section 63 turns on the flag indicative of the first attention function degraded state.

Further alternatively, the estimation section 63 may weigh the results of the first to third processings according to the type of the image displayed on the display section 11. Then, the estimation section 63 may make a majority decision in regard to the weighed results of the first to third processings, and may output a result of the majority decision as the estimation result. For example, in the case where the image displayed on the display section 11 corresponds to the "high visibility image", the estimation section 63 may further weigh the result of the first processing in comparison with the result of the second processing. Meanwhile, in the case where the image displayed on the display section 11 corresponds to the "low visibility image", the estimation section 63 may further weigh the result of the second processing in comparison with the result of the first processing.

[Effects of Embodiment]

As it has been described so far, in the mobile terminal 10 according to the embodiment, the estimation processing section 42 executes the first processing to estimate the user state based on the motion of the user's sightline with respect to the image displayed on the display section 11. Here, there is the correlation between the motion of the user's sightline with respect to the image displayed on the display section 11 and the user state (particularly, the state related to the attention function). Thus, by executing the first processing, it is possible to estimate the user state including the attention function degraded state based on the motion of the user's sightline with respect to the image displayed on the display section 11.

In the mobile terminal 10 according to the embodiment, the estimation processing section 42 executes the first processing in the case where the main task of the user corresponds to the operation of the mobile terminal 10. The estimation processing section 42 does not execute the first processing in the case where the main task of the user does not correspond to the operation of the mobile terminal 10.

In the case where the main task of the user corresponds to the operation of the mobile terminal 10, the user's sightline is likely to be directed to the image displayed on the display section 11 of the mobile terminal 10. Thus, the motion of the user's sightline with respect to the image displayed on the display section 11 is less likely to be inhibited. Meanwhile, in the case where the main task of the user does not correspond to the operation of the mobile terminal 10, the user's sightline is less likely to be directed to the image displayed on the display section 11 of the mobile terminal 10. Thus, the motion of the user's sightline with respect to the image displayed on the display section 11 is likely to be inhibited.

In the case where the main task of the user corresponds to the operation of the mobile terminal 10, the first processing is executed. In the case where the main task of the user does not correspond to the operation of the mobile terminal 10, the first processing is not executed. In this way, it is possible to appropriately execute the first processing that is based on the motion of the user's sightline with respect to the image displayed on the display section 11. As a result, it is possible to appropriately estimate the user state.

In the mobile terminal 10 according to the embodiment, the estimation processing section 42 executes the fourth processing to estimate the user state based on the motion of the user's sightline with respect to the surrounding environment of the user in the case where the main task of the user corresponds to walking. Here, there is the correlation between the motion of the user's sightline with respect to the surrounding environment of the user and the user state (particularly, the state related to the attention function). In addition, in the case where the main task of the user corresponds to walking, the user's sightline is likely to be directed to the surrounding environment of the user. Thus, in the case where the main task of the user corresponds to walking, the fourth processing is executed. In this way, it is possible to appropriately estimate the user state including the attention function degraded state based on the motion of the user's sightline with respect to the surrounding environment of the user. As a result, it is possible to appropriately estimate the user state.

In the mobile terminal 10 according to the embodiment, in the first processing, it is possible to appropriately estimate the user state based on the top-down attention source amount and the bottom-up attention source amount of the user. As a result, it is possible to appropriately estimate the user state. The same can be said for the fourth processing.

In the mobile terminal 10 according to the embodiment, the top-down measurement section 61 is provided with the point of interest detection section 611 and the top-down index deriving section 612. In this way, it is possible to appropriately derive the first top-down index value TD1 based on the motion of the user's sightline with respect to the point of interest in the image displayed on the display section 11. As a result, it is possible to appropriately estimate the user state. The same can be said for the second top-down index value TD2.

In the mobile terminal 10 according to the embodiment, the bottom-up measurement section 62 is provided with the saliency detection section 621 and the bottom-up index deriving section 622. In this way, it is possible to appropriately derive the first bottom-up index value BU1 based on the motion of the user's sightline with respect to the distribution of the saliency in the image displayed on the display section 11. As a result, it is possible to appropriately estimate the user state. The same can be said for the second bottom-up index value BU2.

(Operation of Control Section)

In the mobile terminal 10 according to the embodiment, the control section 31 performs the operation that corresponds to the user state estimated by the state estimation section 40. For example, in the case where the state estimation section 40 estimates that the user state is the first attention function degraded state, the control section 31 performs first operation that corresponds to the first attention function degraded state. Meanwhile, in the case where the state estimation section 40 estimates that the user state is the second attention function degraded state, the control section 31 performs second operation that corresponds to the second attention function degraded state. The control section 31 may transmit information on the estimation result by the state estimation section 40 to the outside through the communication section 24.

[Specific Example of First Operation]

Examples of the first operation are operation to recover from the degraded attention function of the user and operation to output first notification information indicating that the user state is the first attention function degraded state. Example of the operation to recover from the degraded attention function of the user are operation to output warning information that urges the user to take a rest and operation to output reminder information that urges the user to concentrate on the operation of the mobile terminal 10. Example of the operation to output the warning information are operation to output an image of the warning information from the display section 11 by outputting the warning information to the display section 11, and operation to output the voice or other audible warning information from the speaker 12 by outputting the warning information from the speaker 12. The same applies to the reminder information and the first notification information. Another example of the operation to output the first notification information is operation to transmit the first notification information to another information terminal by outputting the first notification information to the communication section 24.

[Specific Example of Second Operation]

Examples of the second operation are operation to output second notification information indicating that the user state is the second attention function degraded state, and operation to notify a person(s) around the mobile terminal 10 that the user state is the second attention function degraded state. Examples of the operation to output the second notification information are operation to output an image of the second notification information from the display section 11 by outputting the second notification information to the display section 11, operation to output the voice second notification information from the speaker 12 by outputting the second notification information to the speaker 12, and operation to transmit the second notification information to the other information terminal by outputting the second notification information to the communication section 24. An example of the operation to notify the person(s) around the mobile terminal 10 that the user state is the second attention function degraded state is operation to blink a light of the mobile terminal 10.

(Modified Example of Bottom-Up Index Deriving Section)

In the first processing, the bottom-up index deriving section 622 may derive the first bottom-up index value BU1 for each predetermined measurement period as follows.

First, the bottom-up index deriving section 622 extracts the two or more saliency maps D40 in the measurement period from the plural saliency maps D40 that are arranged in the chronological order. Then, based on the direction of the user's sightline detected by the sightline detection section 41, the bottom-up index deriving section 622 detects the focus point in each of two or more saliency maps D40 in the measurement period.

Next, the bottom-up index deriving section 622 determines whether the focus point, which is detected from each of the saliency maps D40 in the measurement period, matches the high visibility point in saliency map D40.

Then, the bottom-up index deriving section 622 derives the first bottom-up index value BU1 based on the result of the matching determination between the focus point and the high visibility point. For example, the first bottom-up index value BU1 is a value that corresponds to a ratio of the number of the focus points matching the high visibility points to the total number of the focus points in the measurement period (hereinafter described as a "high visibility matching ratio"). This high visibility matching ratio is an example of the matching degree between the high visibility point and the user's sightline.

In the fourth processing, the bottom-up index deriving section 622 may derive the second bottom-up index value BU2 for each predetermined measurement period by a similar procedure to the procedure in the above first processing.

(First Modified Example of Embodiment)

Next, a description will be made on a mobile terminal 10 according to a first modified example of the embodiment. In the mobile terminal 10 according to the first modified example of the embodiment, the operation of the estimation processing section 42 differs from that in the mobile terminal 10 according to the embodiment.

In the first modified example of the embodiment, in the case where the main task of the user corresponds to the operation of the mobile terminal 10, the estimation processing section 42 selectively executes the first processing or the second processing according to the likeliness of occurrence of the user's bottom-up attention with respect to the image displayed on the display section 11. More specifically, the estimation processing section 42 selectively executes the first processing or the second processing according to the high visibility proportion (the proportion of the high visibility point in the image) in the image displayed on the display section 11. In the case where the high visibility proportion in the image displayed on the display section 11 exceeds the high visibility proportion threshold, the estimation processing section 42 executes the first processing. On the other hand, in the case where the high visibility proportion in the image displayed on the display section 11 does not exceed the high visibility proportion threshold, the estimation processing section 42 executes the second processing.

In this example, in the case where the main task of the user detected by the main task detection section 51 corresponds to the operation of the mobile terminal 10, the estimation section 63 selectively executes the first processing or the second processing based on the detection result by the image type detection section 52. In the case where the type of the image detected by the image type detection section 52 (the image displayed on the display section 11) corresponds to the "high visibility image", the estimation section 63 executes the first processing. On the other hand, in the case where the type of the image detected by the image type detection section 52 corresponds to the "low visibility image", the estimation section 63 executes the second processing.

[Effects of First Modified Example of Embodiment]

As it has been described so far, in the mobile terminal 10 according to the first modified example of the embodiment, the estimation processing section 42 selectively executes the first processing or the second processing according to the likeliness of occurrence of the user's bottom-up attention with respect to the image displayed on the display section 11. More specifically, in the case where the user's bottom-up attention with respect to the image displayed on the display section 11 is likely to occur (in this example, in the case where the image displayed on the display section 11 corresponds to the high visibility image), the estimation processing section 42 executes the first processing. Meanwhile, in the case where the user's bottom-up attention with respect to the image displayed on the display section 11 is less likely to occur (in this example, in the case where the image displayed on the display section 11 corresponds to the low visibility image), the estimation processing section 42 executes the second processing.

In the case where the user's bottom-up attention with respect to the image displayed on the display section 11 is likely to occur, it is possible to accurately execute the first processing to estimate the user state based on the motion of the user's sightline with respect to the image displayed on the display section 11. On the other hand, in the case where the user's bottom-up attention with respect to the image displayed on the display section 11 is less likely to occur, it is difficult to accurately execute the first processing.

Accordingly, when the likeliness of occurrence of the user's bottom-up attention with respect to the image displayed on the display section 11 is considered, it is possible to appropriately execute the first processing to estimate the user state based on the motion of the user's sightline with respect to the image displayed on the display section 11 and the second processing to estimate the user state based on the cognitive response time of the user. As a result, it is possible to appropriately estimate the user state.

(Second Modified Example of Embodiment)

Next, a description will be made on a mobile terminal 10 according to a second modified example of the embodiment. In the mobile terminal 10 according to the second modified example of the embodiment, the operation of the estimation processing section 42 differs from that in the mobile terminal 10 according to the embodiment.

In the second modified example of the embodiment, the estimation processing section 42 executes the first processing not only in the case where the main task of the user corresponds to the operation of the mobile terminal 10 but also in the case where the main task of the user does not correspond to the operation of the mobile terminal 10. A condition to estimate that the user state is the attention function degraded state in the first processing is stricter in the case where the main task of the user does not correspond to the operation of the mobile terminal 10 than in the case where the main task of the user corresponds to the operation of the mobile terminal 10. For example, the first bottom-up threshold BUth1 in the first processing, which is executed in the case where the main task of the user does not correspond to the operation of the mobile terminal 10, is larger than the first bottom-up threshold BUth1 in the first processing, which is executed in the case where the main task of the user corresponds to the operation of the mobile terminal 10. For example, the estimation section 63 adjusts the condition to estimate that the user state is the attention function degraded state in the first processing.

(Effects of Second Modified Example of Embodiment)

As it has been described so far, in the mobile terminal 10 according to the second modified example of the embodiment, the condition to estimate that the user state is the attention function degraded state in the first processing is stricter in the case where the main task of the user does not correspond to the operation of the mobile terminal 10 than in the case where the main task of the user corresponds to the operation of the mobile terminal 10. In the case where the main task of the user does not correspond to the operation of the mobile terminal 10, the motion of the user's sightline with respect to the image displayed on the display section 11 of the mobile terminal 10 is likely to be inhibited. Accordingly, an error is likely to occur to the estimation of the user state in the first processing. Thus, when the condition (the condition to estimate that the user state is the attention function degraded state) in the first processing, which is executed in the case where the main task of the user does not correspond to the operation of the mobile terminal 10, is set to be stricter than the condition in the first processing, which is executed in the case where the main task of the user corresponds to the operation of the mobile terminal 10, it is possible to reduce a chance of the erroneous estimation of the user state in the first processing. As a result, it is possible to appropriately estimate the user state.

(Other Embodiments)

In the description that has been made so far, the case where the estimation processing section 42 executes the first to sixth processings has been exemplified. However, the technique disclosed herein is not limited thereto. For example, any of the first to sixth processings may not be executed, or another processing may be executed in addition to the first to sixth processings.

The case where the first processing, the second processing, and the third processing are executed when the main task of the user corresponds to the operation of the mobile terminal 10 has been exemplified. However, the technique disclosed herein is not limited thereto. For example, the estimation processing section 42 may be configured to execute the first processing, the second processing, and the third processing not only in the case where the main task of the user corresponds to the operation of the mobile terminal 10 but also in the case where the main task of the user does not correspond to the operation of the mobile terminal 10.

The case where the fourth processing, the fifth processing, and the sixth processing are executed when the main task of the user corresponds to walking has been exemplified. However, the technique disclosed herein is not limited thereto. For example, the estimation processing section 42 may be configured to execute the fourth processing, the fifth processing, and the sixth processing not only in the case where the main task of the user corresponds to walking but also in the case where the main task of the user does not correspond to walking.

In the description that has been described so far, the case where the mobile terminal 10 constitutes the smartphone has been exemplified. However, the technique disclosed herein is not limited thereto. For example, the mobile terminal 10 may be a tablet computer or another mobile-type information terminal.

In the description that has been made so far, the case where the estimation section 63 estimates the user state at the estimation intervals has been exemplified. However, the technique disclosed herein is not limited thereto. For example, the estimation section 63 may be configured to estimate a short-term state of the user as described above, or may be configured to estimate a long-term state of the user. Examples of the long-term state of the user are a state of the disease where a symptom gradually progresses and a state of a degraded function due to aging.

In the description that has been made so far, the case where the estimation section 63 estimates the function degraded states (more specifically, the attention function degraded state, the motor function degraded state, and the cognitive motor function degraded state) and the normal state has been exemplified. However, the technique disclosed herein is not limited thereto. For example, the estimation section 63 may be configured to estimate a negative state of the user such as the above function degraded state, or may be configured to estimate a positive state of the user. Examples of the positive state of the user are: a state where the user is recovered from the function degraded state to the normal state; and a state where the normal state is maintained.

In the description that has been made so far, the case where the image data acquired by the front camera 21 and the image data acquired by the rear camera 22 are used has been exemplified. However, the technique disclosed herein is not limited thereto. For example, the controller 30 may be configured to use the image data that is input to display equipment and the image data that is acquired by a camera capturing an image of a target person (a target person who can be the user) who sees the image displayed on the display equipment. Examples of the display equipment are a smartphone, a personal computer, and a television receiver. Alternatively, the controller 30 may be configured to use image data that is acquired by a monitoring camera and image data that is acquired by a camera capturing an image of a target person who sees the environment captured by the monitoring camera. The monitoring camera is provided to a waiting room of a hospital, a monitoring room for a security guard, a cash register at a store, inside of the building, a street, or the like.

In the description that has been made so far, the reference values such as the top-down threshold and the bottom-up threshold that serve as determination criteria may be set per user. More specifically, the above reference values may be set or adjusted based on a learning result of information unique to the user such as experience of the user and regular behavior of the user. An example of the experience of the user is a traveling frequency on a road. For example, the above reference values may be set or adjusted based on whether the road on which the user walks is the road on which the user is used to walk or the road on which the user walks for the first time. Examples of the regular behavior of the user are average behavior of the user in a long period such as one week or one month and behavior of the user in a period in which the user is estimated to be in the normal state by another method. An example of the behavior of the user is a moving speed of the user's sightline with respect to the high visibility point and/or the point of interest.

The above reference values may be set based on a database that stores various types of data on persons. In such a database, age, a physical characteristic, a physical function, a personality, culture, lifestyle, and the like of each of the persons are stored in a mutually correlated manner. For example, a data group related to persons having a specific characteristic may be extracted from the data group stored in the database, and the above reference values may be set based on the extracted data group. Examples of the data group that is extracted from the data group stored in the database are a data group related to healthy persons and a data group related to persons having a specific disease. Alternatively, the above reference values may be set based on information that is acquired by different equipment (for example, another smartphone) from the controller 30.

The following description relates to a computer environment in which embodiments of the present disclosure may be implemented. This environment may include an embedded computer environment, local multi-processor embodiment, remote (e.g., cloud-based) environment, or a mixture of all the environments.

Figure 23:
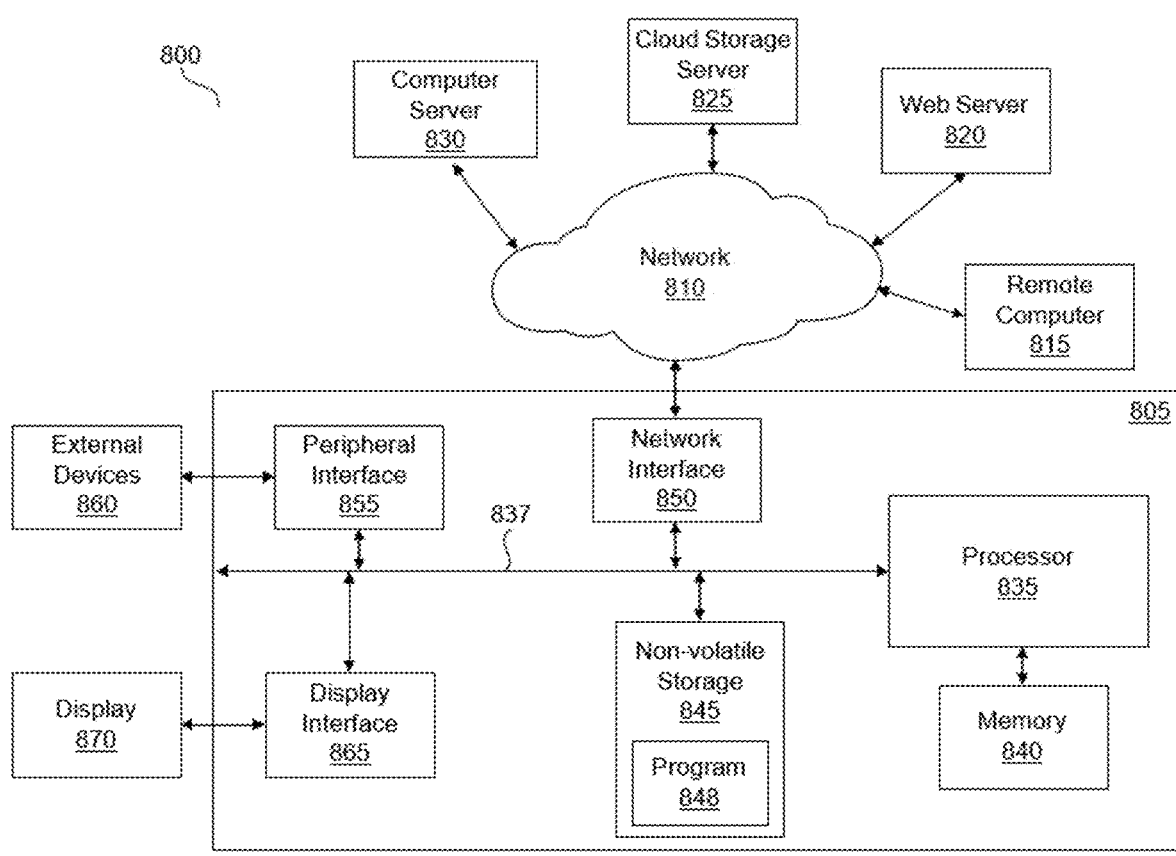
FIG. 23 is a block diagram of computer-based circuitry that may be used to implement control features of the present disclosure.

FIG. 23 illustrates a block diagram of a computer that may implement the various embodiments described herein. The present disclosure may be embodied as a system, a method, and/or a computer program product. The computer program product may include a computer readable storage medium on which computer readable program instructions are recorded that may cause one or more processors to carry out aspects of the embodiment.

The non-transitory computer readable storage medium may be a tangible device that can store instructions for use by an instruction execution device (processor). The computer readable storage medium may be, for example, but is not limited to, an electronic storage device, a magnetic storage device, an optical storage device, an electromagnetic storage device, a semiconductor storage device, or any appropriate combination of these devices. A non-exhaustive list of more specific examples of the computer readable storage medium includes each of the following (and appropriate combinations): flexible disk, hard disk, solid-state drive (SSD), random access memory (RAM), read-only memory (ROM), erasable programmable read-only memory (EPROM or Flash), static random-access memory (SRAM), compact disc (CD or CD-ROM), digital versatile disk (DVD) and memory card or stick. A computer readable storage medium, as used in this disclosure, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described in this disclosure can be downloaded to an appropriate computing or processing device from a computer readable storage medium or to an external computer or external storage device via a global network (i.e., the Internet), a local area network, a wide area network and/or a wireless network. The network may include copper transmission wires, optical communication fibers, wireless transmission, routers, firewalls, switches, gateway computers and/or edge servers. A network adapter card or network interface in each computing or processing device may receive computer readable program instructions from the network and forward the computer readable program instructions for storage in a computer readable storage medium within the computing or processing device.

Computer readable program instructions for carrying out operations of the present disclosure may include machine language instructions and/or microcode, which may be compiled or interpreted from source code written in any combination of one or more programming languages, including assembly language, Basic, Fortran, Java, Python, R, C, C++, C #, or similar programming languages. The computer readable program instructions may execute entirely on a user's personal computer, notebook computer, tablet, or smartphone, entirely on a remote computer or compute server, or any combination of these computing devices. The remote computer or compute server may be connected to the user's device or devices through a computer network, including a local area network or a wide area network, or a global network (i.e., the Internet). In some embodiments, electronic circuitry including, for example, programmable logic circuitry, field-programmable gate arrays (FPGA), or programmable logic arrays (PLA) may execute the computer readable program instructions by using information from the computer readable program instructions to configure or customize the electronic circuitry, in order to perform aspects of the present disclosure.

Aspects of the present disclosure are described herein with reference to flow diagrams and block diagrams of methods, apparatus (systems), and computer program products according to embodiments of the disclosure. It will be understood by those skilled in the art that each block of the flow diagrams and block diagrams, and combinations of blocks in the flow diagrams and block diagrams, can be implemented by computer readable program instructions.

The computer readable program instructions that may implement the systems and methods described in this disclosure may be provided to one or more processors (and/or one or more cores within a processor) of a general purpose computer, special purpose computer, or other programmable apparatus to produce a machine, such that the instructions, which execute via the processor of the computer or other programmable apparatus, create a system for implementing the functions specified in the flow diagrams and block diagrams in the present disclosure. These computer readable program instructions may also be stored in a computer readable storage medium that can direct a computer, a programmable apparatus, and/or other devices to function in a particular manner, such that the computer readable storage medium having stored instructions is an article of manufacture including instructions which implement aspects of the functions specified in the flow diagrams and block diagrams in the present disclosure.

The computer readable program instructions may also be loaded onto a computer, other programmable apparatus, or other device to cause a series of operational steps to be performed on the computer, other programmable apparatus, or other device to produce a computer implemented process, such that the instructions which execute on the computer, other programmable apparatus, or other device implement the functions specified in the flow diagrams and block diagrams in the present disclosure.

FIG. 23 is a functional block diagram illustrating a networked system 800 of one or more networked computers and servers. In an embodiment, the hardware and software environment illustrated in FIG. 23 may provide an exemplary platform for implementation of the software and/or methods according to the present disclosure.

Referring to FIG. 23, a networked system 800 may include, but is not limited to, computer 805, network 810, remote computer 815, web server 820, cloud storage server 825 and computer server 830. In some embodiments, multiple instances of one or more of the functional blocks illustrated in FIG. 3 may be employed.

Additional detail of computer 805 is shown in FIG. 23. The functional blocks illustrated within computer 805 are provided only to establish exemplary functionality and are not intended to be exhaustive. And while details are not provided for remote computer 815, web server 820, cloud storage server 825 and compute server 830, these other computers and devices may include similar functionality to that shown for computer 805.

Computer 805 may be built into the automobile, a personal computer (PC), a desktop computer, laptop computer, tablet computer, netbook computer, a personal digital assistant (PDA), a smart phone, or any other programmable electronic device capable of communicating with other devices on network 810.

Computer 805 may include processor 835, bus 837, memory 840, non-volatile storage 845, network interface 850, peripheral interface 855 and display interface 865. Each of these functions may be implemented, in some embodiments, as individual electronic subsystems (integrated circuit chip or combination of chips and associated devices), or, in other embodiments, some combination of functions may be implemented on a single chip (sometimes called a system on chip or SoC).

Processor 835 may be one or more single or multi-chip microprocessors, such as those designed and/or manufactured by Intel Corporation, Advanced Micro Devices, Inc. (AMD), Arm Holdings (Arm), Apple Computer, etc. Examples of microprocessors include Celeron, Pentium, Core i3, Core i5 and Core i7 from Intel Corporation; Opteron, Phenom, Athlon, Turion and Ryzen from AMD; and Cortex-A, Cortex-R and Cortex-M from Arm.

Bus 837 may be a proprietary or industry standard high-speed parallel or serial peripheral interconnect bus, such as ISA, PCI, PCI Express (PCI-e), AGP, and the like.

Memory 840 and non-volatile storage 845 may be computer-readable storage media. Memory 840 may include any suitable volatile storage devices such as Dynamic Random-Access Memory (DRAM) and Static Random-Access Memory (SRAM). Non-volatile storage 845 may include one or more of the following: flexible disk, hard disk, solid-state drive (SSD), read-only memory (ROM), erasable programmable read-only memory (EPROM or Flash), compact disc (CD or CD-ROM), digital versatile disk (DVD) and memory card or stick.

Program 848 may be a collection of machine-readable instructions and/or data that is stored in non-volatile storage 845 and is used to create, manage, and control certain software functions that are discussed in detail elsewhere in the present disclosure and illustrated in the drawings. In some embodiments, memory 840 may be considerably faster than non-volatile storage 845. In such embodiments, program 848 may be transferred from non-volatile storage 845 to memory 840 prior to execution by processor 835.

Computer 805 may be capable of communicating and interacting with other computers via network 810 through network interface 850. Network 810 may be, for example, a local area network (LAN), a wide area network (WAN) such as the Internet, or a combination of the two, and may include wired, wireless, or fiber optic connections. In general, network 810 can be any combination of connections and protocols that support communications between two or more computers and related devices.

Peripheral interface 855 may allow for input and output of data with other devices that may be connected locally with computer 805. For example, peripheral interface 855 may provide a connection to external devices 860. External devices 860 may include input devices, e.g., any or all of the devices in the information acquisition means 10 and/or other suitable input devices, and output devices, e.g., any or all various actuator devices AC and/or other suitable output devices, e.g., a speaker. External devices 860 may also include portable computer-readable storage media such as, for example, thumb drives, portable optical or magnetic disks, and memory cards. Software and data used to practice embodiments of the present disclosure, for example, program 848, may be stored on such portable computer-readable storage media. In such embodiments, software may be loaded onto non-volatile storage 845 or, alternatively, directly into memory 840 via peripheral interface 855. Peripheral interface 855 may use an industry standard connection, such as RS-232 or Universal Serial Bus (USB), to connect with external devices 860.

Display interface 865 may connect computer 805 to display 870, e.g., a head-up display or a screen of a car navigation system. Display 870 may be used, in some embodiments, to present a command line or graphical user interface to a user of computer 805. Display interface 865 may connect to display 870 using one or more proprietary or industry standard connections, such as VGA, DVI, DisplayPort and HDMI.

As described above, network interface 850, provides for communications with other computing and storage systems or devices external to computer 805. Software programs and data discussed herein may be downloaded from, for example, remote computer 815, web server 820, cloud storage server 825 and compute server 830 to non-volatile storage 845 through network interface 850 and network 810. Furthermore, the systems and methods described in this disclosure may be executed by one or more computers connected to computer 805 through network interface 850 and network 810. For example, in some embodiments the systems and methods described in this disclosure may be executed by remote computer 815, computer server 830, or a combination of the interconnected computers on network 810.

Data, datasets and/or databases employed in embodiments of the systems and methods described in this disclosure may be stored and or downloaded from remote computer 815, web server 820, cloud storage server 825 and compute server 830.

The embodiments that have been described herein may appropriately be combined and implemented. Each of the embodiments that has been described so far is essentially and merely illustrative and thus has no intention to limit the scopes of the present invention, application subjects thereof, and application thereof.

DESCRIPTION OF REFERENCE SIGNS AND NUMERALS

10 Mobile terminal
11 Display section
12 Speaker
13 Storage section
21 Front camera
22 Rear camera
23 Operation section
24 Communication section
25 Microphone
26 Location sensor
27 State sensor
28 Environment sensor
30 Controller (state estimation device)
31 Control section
40 State estimation section
41 Sightline detection section
42 Estimation processing section
50 Image acquisition section
51 Main task detection section
52 Image type detection section
53 Time detection section
54 Erroneous operation detection section 55 Walking pace detection section
56 Wobbling detection section
61 Top-down measurement section
62 Bottom-up measurement section
63 Estimation section
611 Point of interest detection section
612 Top-down index deriving section
621 Saliency detection section
622 Bottom-up index deriving section

The invention claimed is:

1. A device that estimates a state of a user of a mobile terminal having a display for displaying an image, the state estimation device comprising
a sightline detector that detects a sightline of the user; and processing circuitry configured to:
determine a top-down index value based on the image displayed on the display and the sightline of the user detected by the sightline detector, the top-down index value being correlated with an attention source amount that is allocated to top-down attention of the user with respect to the image on the display;
determine a bottom-up index value based on the image displayed on the display and the sightline of the user detected by the sightline detection, the bottom-up index value being correlated with the attention source amount that is allocated to bottom-up attention of the user with respect to the image on the display; and
estimate the state of the user including an attention function degraded state based on the top-down index value and the bottom-up index value, wherein
on condition that the top-down index value falls below a predetermined top-down threshold, the processing circuitry is configured to:
estimate that the user is in a first attention function degraded state when the bottom-up index value does not fall below a predetermined bottom-up threshold, and
estimate that the user is in a second attention function degraded state, in which an attention function is degraded in comparison with that in the first attention function degraded state, when the bottom-up index value falls below the bottom-up threshold.

2. The device according to claim 1, wherein
the processing circuitry is configured to
determine a point of interest in the image displayed on the display; and
further determine the top-down index value based on motion of the sightline of the user with respect to the point of interest in the image.

3. The device according to claim 2, wherein
the processing circuitry configured to:
determine distribution of saliency in the image displayed on the display; and
further determine the bottom-up index value based on motion of the sightline of the user with respect to the distribution of the saliency in the image.

4. The device according to claim 1, wherein
the processing circuitry is configured to further estimate the user state based on one of the image displayed on the display or a surrounding environment, and the sightline of the user detected by the sightline detector and a cognitive response time of the user.

5. The device according to claim 4, wherein
the processing circuitry is configured to selectively further estimate the user state based on one of the image displayed on the display or a surrounding environment according to likeliness of occurrence of bottom-up attention of the user with respect to the image displayed on the display.

6. The device according to claim 1, wherein the attention function degraded state includes:
a first attention function degraded state that is at least one of wakefulness degradation, fatigue, and a drifted state; and
a second attention function degraded state that is at least one of a cardiac disorder, a brain disorder, epilepsy, and hypoglycemia.

7. The device according to claim 3, wherein
the processing circuitry is configured to further estimate the user state based on one of the image displayed on the display or a surrounding environment, and the sightline of the user detected by the sightline detector and a cognitive response time of the user.

8. The device according to claim 7, wherein
the processing circuitry is configured to selectively further estimate the user state based on one of the image displayed on the display or a surrounding environment according to likeliness of occurrence of bottom-up attention of the user with respect to the image displayed on the display.

9. The device according to claim 2, wherein
the processing circuitry is configured to further estimate the user state based on one of the image displayed on the display or a surrounding environment, and the sightline of the user detected by the sightline detector and a cognitive response time of the user.

10. The device according to claim 1, wherein
the processing circuitry configured to:
determine distribution of saliency in the image displayed on the display; and
further determine the bottom-up index value based on motion of the user's sightline with respect to the distribution of the saliency in the image.

11. The device according to claim 10, wherein
the processing circuitry is configured to further estimate the user state based on one of the image displayed on the display or a surrounding environment, and the sightline of the user detected by the sightline detector and a cognitive response time of the user.

12. The device according to claim 1, wherein the processing circuitry is configured to selectively further estimate the user state based on one of the image displayed on the display or a surrounding environment according to likeliness of occurrence of bottom-up attention of the user with respect to the image displayed on the display.

13. A method of estimating a state of a user of a mobile terminal having a display for displaying an image, the method comprising:
detecting a sightline of the user;
determining a top-down index value based on the image displayed on the display and the sightline of the user, the top-down index value being correlated with an attention source amount that is allocated to top-down attention of the user with respect to the image on the display;
determining a bottom-up index value based on the image displayed on the display and the sightline of the user detected by the sightline detection, the bottom-up index value being correlated with the attention source amount that is allocated to bottom-up attention of the user with respect to the image on the display; and estimating the state of the user including an attention function degraded state based on the top-down index value and the bottom-up index value, wherein
    on condition that the top-down index value falls below a predetermined top-down threshold,
        estimating that the user is in a first attention function degraded state when the bottom-up index value does not fall below a predetermined bottom-up threshold, and
        estimating that the user is in a second attention function degraded state, in which an attention function is degraded in comparison with that in the first attention function degraded state, when the bottom-up index value falls below the bottom-up threshold.

14. A non-transitory computer readable storage device having computer readable instructions that when executed by a controller including a computer cause the computer to execute a state of a user of a mobile terminal estimation method, the method comprising:
    detecting a sightline of the user;
    determining a top-down index value based on an image displayed on the display and the sightline of the user detected, the top-down index value being correlated with an attention source amount that is allocated to top-down attention of the user with respect to the image on the display;
    determining a bottom-up index value based on the image displayed on the display and the sightline of the user detected by the sightline detection, the bottom-up index value being correlated with the attention source amount that is allocated to bottom-up attention of the user with respect to the image on the display; and
    estimating the state of the user including an attention inaction degraded state based on the top-down index value and the bottom-up index value, wherein
    on condition that the top-down index value falls below a predetermined top-down threshold,
    estimating that the user is in a first attention function degraded state when the bottom-up index value does not fall below a predetermined bottom-up threshold, and
    estimating that the user is in a second attention function degraded state, in which an attention function is degraded in comparison with that in the first attention function degraded state, when the bottom-up index value falls below the bottom-up threshold.

\* \* \* \* \*